United States Patent
Cha et al.

(10) Patent No.: US 12,252,711 B2
(45) Date of Patent: Mar. 18, 2025

(54) OSTEOPOROSIS MODEL COMPRISING CALCIUM PHOSPHATE HYDROGEL COMPOSITION AND USE THEREOF

(71) Applicant: MEDIFAB CO., LTD., Seoul (KR)

(72) Inventors: Mi Sun Cha, Seoul (KR); Jung Ju Kim, Ansan-si (KR)

(73) Assignee: MEDIFAB CO., LTD., Seoul (KR)

( * ) Notice: Subject to any disclaimer, the term of this patent is extended or adjusted under 35 U.S.C. 154(b) by 392 days.

(21) Appl. No.: 17/311,814

(22) PCT Filed: Jul. 23, 2020

(86) PCT No.: PCT/KR2020/009694
§ 371 (c)(1),
(2) Date: Jun. 8, 2021

(87) PCT Pub. No.: WO2021/015562
PCT Pub. Date: Jan. 28, 2021

(65) Prior Publication Data
US 2022/0145254 A1  May 12, 2022

(30) Foreign Application Priority Data

Jul. 25, 2019 (KR) .................. 10-2019-0090487
Jul. 25, 2019 (KR) .................. 10-2019-0090492

(51) Int. Cl.
*G01N 33/84* (2006.01)
*A61L 27/52* (2006.01)
(Continued)

(52) U.S. Cl.
CPC ......... *C12N 5/0654* (2013.01); *C12N 5/0662* (2013.01); *G01N 33/5038* (2013.01);
(Continued)

(58) Field of Classification Search
CPC .............. C08J 3/075; C08L 5/08; C08L 89/00
See application file for complete search history.

(56) References Cited

U.S. PATENT DOCUMENTS 8,690,874 B2 * 4/2014 Thorne ................. A61L 27/227
606/86 R
2007/0092580 A1 * 4/2007 Chow .................... A61L 27/54
424/602

FOREIGN PATENT DOCUMENTS

JP   H0-7194373 A    8/1995
JP   2013-063940 A   4/2013
(Continued)

OTHER PUBLICATIONS

Soto-Sierra et al. [Algal Research 36 (2018) 175-192] Extraction and fractionation of micro algae based protein products (Year: 2018).*
(Continued)

*Primary Examiner* — Catherine S Branch
*Assistant Examiner* — Olga Lucia Donahue
(74) *Attorney, Agent, or Firm* — Fitch, Even, Tabin & Flannery LLP

(57) ABSTRACT

Provided is a method of preparing a hydrogel composition including a uniform content of calcium phosphate, wherein a hydrogel composition prepared by the method has a uniform content of calcium phosphate, and thus may be used to quantify phosphates contained in the hydrogel composition. Provided is an in-vitro 3D osteoporosis model including a calcium phosphate hydrogel composition, wherein osteoblasts and osteoclasts may be three-dimensionally co-cultured inside a biogel, such that the osteoporosis model may be fabricated according to an intended use or clinical stage. Further, the model contains a calcium phosphate hydrogel with a uniform content of phosphate and thus enables quantification of calcium phosphate through mea-
(Continued)

surement of phosphates, and therefore, the model may be used to screen candidate compounds for an osteoporosis drug and may effectively predict therapeutic effects of the drug on osteoporosis.

6 Claims, 26 Drawing Sheets

(51) Int. Cl.
    *C12N 5/077*     (2010.01)
    *C12N 5/0775*     (2010.01)
    *G01N 33/50*     (2006.01)

(52) U.S. Cl.
    CPC ......... *G01N 33/5088* (2013.01); *G01N 33/84* (2013.01); *C12N 2501/25* (2013.01); *C12N 2502/1142* (2013.01); *C12N 2502/1311* (2013.01); *C12N 2506/1346* (2013.01); *C12N 2513/00* (2013.01); *C12N 2533/18* (2013.01); *C12N 2533/54* (2013.01); *C12N 2533/74* (2013.01); *C12N 2537/10* (2013.01)

(56) References Cited

FOREIGN PATENT DOCUMENTS

| JP | 2013-530021 A | 7/2013 |
|---|---|---|
| JP | 2017-524671 A | 8/2017 |
| KR | 10-2008-0096746 A | 11/2008 |
| KR | 10-2015-0087458 A | 7/2015 |
| KR | 10-2017-0078417 A | 7/2017 |
| KR | 10-2019-0035051 A | 4/2019 |
| KR | 10-2095485 B1 | 3/2020 |
| KR | 10-2105549 B1 | 4/2020 |
| WO | 2012/003326 A1 | 1/2012 |
| WO | 2015/195701 A1 | 12/2015 |

OTHER PUBLICATIONS

KIPO, Application No. PCT/KR2020/009694; International Search Report dated Oct. 27, 2020.

Cha, Chaenyung et al., "Integrative design of a poly(ethylene glycol)-poly(propylene glycol)-alginate hydrogel to control three dimensional biomineralization," Biomaterials, 2011, vol. 32, pp. 2695-2703.

Elango, Jeevithan et al., "Chitosan-Collagen 3D Matrix Mimics Trabecular Bone and Regulates RANKL-Mediated Paracrine Cues of Differentiated Osteoblast and Mesenchymal Stem Cells for Bone Marrow Macrophage-Derived Osteoclastogenesis," Biomolecules, 2019, vol. 9, No. 173 (20 pages).

Ito, Tomoko et al., "Preparation of injectable auto-forming alginate gel containing simvastatin with amorphous calcium phosphate as a controlled release medium and their therapeutic effect in osteoporosis model rat," Journal of Materials Science: Materials in Medicine, 2012, vol. 23, pp. 1291-1297.

Owen, Robert et al., "In vitro models for studying bone remodelling," Frontiers in Bioengineering and Biotechnology, 2018, vol. 6 (52 pages).

Tangprasert, Atsadaporn et al., "Mimicked extracellular matrix of calcified soft tissue based on chitosan/gelatin/compounded calcium phosphate hydrogel to design ex vivo model for heterotopic ossification," Materials and Design, 2017, vol. 134, pp. 486-493.

Zhao, Qiang et al., "Polysaccharide-based biomaterials with on-demand nitric oxide releasing property regulated by enzyme catalysis," Biomaterials, 2013, vol. 34, pp. 8450-8458.

\* cited by examiner

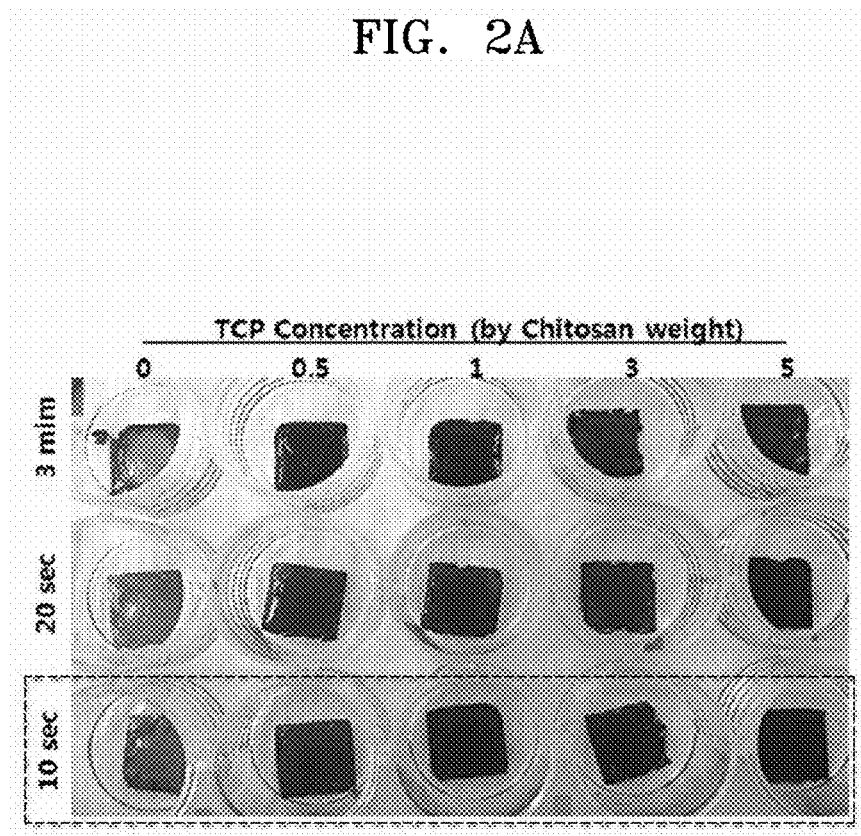

TCP Bead Size: 3mm ± 0.5mm

OSTEOPOROSIS MODEL COMPRISING CALCIUM PHOSPHATE HYDROGEL COMPOSITION AND USE THEREOF

CROSS-REFERENCE TO RELATED APPLICATIONS

This application is a U.S. national phase application filed under 35 U.S.C. § 371 of International Application No. PCT/KR2020/009694, filed Jul. 23, 2020, designating the United States, which claims priority from Korean Application No. 10-2019-0090492 and Korean Application No. 10-2019-0090487, both filed Jul. 25, 2019.

TECHNICAL

The present application claims the benefit of Korean Patent Applications Nos. 10-2019-0090487 and 10-2019-0090492 filed on Jul. 25, 2019, in the Korean Intellectual Property Office, and the entire disclosure of the above specifications is incorporated by reference in the present application.

The present disclosure relates to a method of preparing a hydrogel composition containing a uniform content of calcium phosphate, an osteoporosis model including a calcium phosphate hydrogel composition, and a use thereof.

BACKGROUND

Osteoporosis, which is a skeletal disease in which bones become prone to fracture due to reduced bone strength, is recognized as an age-related disease, and due to the aging of populations, has risen as an important issue in the health care field globally. Given the rapid aging of the South Korean population, the number of osteoporosis patients in South Korea is expected to rise rapidly. According to the fourth survey of national health and nutrition in South Korea, about 35% of women of 50 years of age or more were reported to suffer from osteoporosis, and this number is expected to continue to rise in the future. With the increase in the number of osteoporosis patients, many drugs have been developed or are under development for the treatment of osteoporosis.

Meanwhile, an animal model refers to the use of an animal during the research of diseases or injury analogous to human conditions, and through the animal model, researchers can apply treatment methods, procedures, etc. that are difficult to perform on humans, and verify their therapeutic effects and the like. Since elements of molecular biology, genetics, and bioengineering are crucial parts of the investigation of a particular disease in medicine, animal models of disease have come to play an important role, and preclinical testing has become an essential step before conducting clinical tests in people to conduct research on a particular disease. However, due to ethical concerns raised over the use of such animal models, there is a need to develop an experiment model that can replace animal models.

SUMMARY

Provided is a method including: preparing a first composition by dissolving chitosan in a gelatin solution; preparing a second composition by dispersing a calcium phosphate in a calcium chloride solution; and mixing the first composition with the second composition, to thereby prepare a calcium phosphate hydrogel composition.

Provided is a hydrogel composition prepared by the method.

Provided is a method of quantifying a calcium phosphate, the method including: dissolving the hydrogel composition in an acidic solution; and measuring a content of phosphate released from the composition.

Provided is a cellular scaffold including: a biogel capable of three-dimensional co-culture of cells; and a calcium phosphate hydrogel composition.

Provided is an osteoporosis model including the cellular scaffold.

Provided is a method of predicting therapeutic effect on osteoporosis, the method including: injecting, in the osteoporosis model, a candidate compound for osteoporosis treatment; and quantifying phosphates inside a calcium phosphate hydrogel.

According to one aspect of the present disclosure, provided is a method including: preparing a first composition by dissolving chitosan in a gelatin solution; preparing a second composition by dispersing calcium phosphate in a calcium chloride solution; and mixing the first composition with the second composition, to thereby prepare a calcium phosphate hydrogel composition.

In the present application, the term "hydrogel" may refer to a three-dimensional network structure formed with hydrophilic polymers crosslinked via covalent or non-covalent bonds. Due to hydrophilicity of the constituent material, in aqueous solutions and aqueous environments, the hydrogel has the ability to absorb a large amount of water and undergoes swelling, but does not dissolve due to its crosslinked structures. As such, hydrogels can be made with various shapes and characteristics depending on the constituent components and preparation method used, and since hydrogels typically retain large quantities of water, they may exhibit characteristics of an intermediate state between liquid and solid.

In the present application, the term "chitosan" may refer to a linear polysaccharide composed of D-glucosamine and N-acetyl glucosamine. The chitosan is represented by Formula 1 below and can be obtained by the treatment of the exoskeleton of certain crustaceans, such as crabs and shrimps, with sodium hydroxide, a base, but is not limited thereto. The chitosan may include chitosan derivatives as well as pure chitosan. For example, the chitosan derivatives may include at least one from phthalated chitosan, esterified chitosan, amidated chitosan, and formylated chitosan.

[Formula 1]

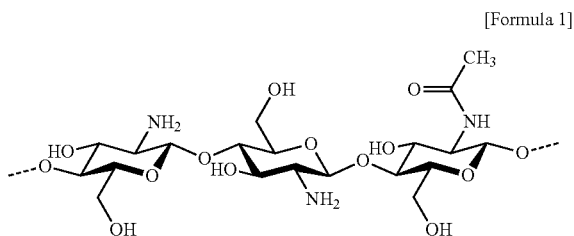

In the present application, the term "calcium phosphate" is used in its general meaning, and three types of calcium phosphate are known, namely, calcium hydrogen phosphate, calcium dihydrogen phosphate, and tricalcium phosphate. In detail, tricalcium phosphate, which is represented by chemical formula $Ca_3(PO_4)_2$, is found in nature as apatite and exists in the bones of mammalian animals, and is also distributed widely in the soil as an essential factor for plant growth. Calcium hydrogen phosphate, also known as dibasic calcium phosphate or calcium monohydrogen phosphate, includes, other than anhydrous forms, $CaHPO_4 \cdot 1.5H_2O$, $CaHPO_4 \cdot 2H_2O$ and $CaHPO_4 \cdot 4.75H_2O$ as hydrated products. In addition, calcium dihydrogen phosphate, which is represented by formula $Ca(H_2PO_4)_2$, is also known as monobasic calcium phosphate. Typically existing as monohydrate, calcium dihydrogen phosphate is a colorless orthorhombic crystal which forms anhydrous products at 100° C. when heated, and decomposes at 152° C. to form calcium metaphosphate $Ca(PO_3)_2$ (melting point 975° C., specific gravity 2.82).

Also, the calcium phosphate may refer to various phosphates of calcium and may be represented by Formula 2 below. The calcium phosphate may be one selected from amorphous calcium phosphate, tricalcium phophate (TCP), and tetracalcium phosphate (TTCP).

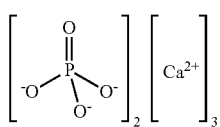

[Formula 2]

The method according to a specific example includes preparing a first composition by dissolving chitosan in a gelatin solution. The chitosan may be included in 0.1 wt % to 10 wt %, 0.1 wt % to 8 wt %, 0.1 wt % to 5 wt %, 0.1 wt % to 0.25 wt %, 0.25 wt % to 0.3 wt %, 0.15 wt % to 0.2 wt %, 1 wt % to 8 wt %, or 1 wt % to 5 wt %, with respect to 100 wt % of the first composition. Here, when the content of chitosan is less than the above ranges, there may be issues where the first composition having too low a viscosity hinders the preparation of hydrogel compositions with uniform shape, and also causes calcium phosphate to be too easily released from the hydrogel composition formed. When the content of chitosan exceeds the above ranges, there may be issues where the first composition having too high a viscosity hinders uniform distributions of calcium phosphate, and also gives rise to air bubble formation, thus making it difficult to prepare hydrogels with uniform shape.

The method according to a specific example includes preparing a second composition by dispersing a calcium phosphate in a calcium chloride solution. The preparation of the second composition may further include sonicating the calcium chloride solution having calcium phosphate dissolved therein. The calcium phosphate may be included in 0.1 wt % to 10 wt %, 0.1 wt % to 8 wt %, 0.1 wt % to 5 wt %, 0.5 wt % to 6 wt %, 0.5 wt % to 3.5 wt %, 4.5 wt % to 7.5 wt %, or 1.5 wt % to 2.5 wt %, with respect to 100 wt % of the second composition. Here, when the content of calcium phosphate is less than the above ranges, there may be issues where a calcium phosphate hydrogel becomes difficult to apply to an osteoporosis model and the like, and the content of calcium phosphate exceeding the above ranges may cause toxicity when applied to cells and animals and also may cause other biological irritations.

The method according to a specific example includes preparing a hydrogel bead composition by adding the hydrogel composition to an alkaline solution in a dropwise manner. The alkaline solution may have a pH of 8 to 11. For example, the alkaline solution may have a pH of 8 to 11, a pH of 8 to 10, a pH of 8 to 9, a pH of 9 to 11, a pH of 9 to 10, or a pH of 10 to 11. Here, when the pH of the solution is less than the above ranges, there may be issues where due to lack of instantaneous crosslinking reactions, the beads are unable to maintain their forms and dissolve in solvent, that is, the alkaline solution. When the pH of the solution exceeds the above ranges, there may be issues where crosslinking occurs too rapidly, thus failing to realize replicable, reproducible shapes of hydrogel, and moreover, pH-induced cytotoxicity may arise when cultured together with cells. Further, the alkaline solution may be, for example, a sodium hydroxide solution, a calcium hydroxide solution, or an ammonia solution, or the like.

According to another aspect of the present disclosure, provided is a calcium phosphate hydrogel composition prepared by the above method. The hydrogel composition may be a hydrogel bead composition. The calcium phosphate may be included in 0.1 wt % to 10 wt % with respect to 100 wt % of the hydrogel composition. For example, the phosphate may be included in 0.1 wt % to 10 wt %, 0.1 wt % to 8 wt %, 0.1 wt % to 5 wt %, 0.5 wt % 8 wt %, 0.5 wt % to 5 wt %, 2.5 wt % to 5 wt %, or 1 wt % to 5 wt %. Here, when the content of phosphate is less than the above ranges, there may be issues where the contact area between osteoclasts and calcium phosphate decreases, thus making it difficult to determine bone resorption effect of the cells. When the content of phosphate exceeds the above ranges, there may be issues where the amount of calcium phosphate contained in the hydrogel becomes oversaturated, thus causing calcium phosphate to leak from the formed hydrogel composition. That is, as the composition contains a uniform content of calcium phosphate, a decrease amount of calcium phosphate can be quantitatively confirmed by measuring the amount of phosphate contained in the hydrogel composition. Further, the hydrogel composition may release calcium ions or phosphate ions. In the in-vivo bone environment, calcium ions and phosphate ions always exist around cells, and hence, the calcium ions and/or phosphate ions released from the hydrogel composition may serve a role to mimic the bone environment in the surrounding cells. Accordingly, the hydrogel composition according to one aspect, capable of mimicking the bone environment, can screen candidate compounds for an osteoporosis drug and can effectively predict therapeutic effect of the drug on osteoporosis.

In addition, the hydrogel composition may be a composition for bio ink. Although the chitosan contained in the hydrogel composition has a relatively high solubility in acidic environments of pH 6 or less, when the content of chitosan is high, as hydrated chitosan polymer bodies have a high viscosity, the hydrogel composition may be utilized as ink for 3D printing.

According to another aspect, provided is a method of quantifying calcium phosphate, the method including: dissolving the hydrogel composition in an acidic solution; and measuring the content of phosphate released from the hydrogel composition. The acidic solution may be a hydrogen chloride solution, a nitric acid solution, a sulfuric acid solution, an acetic acid solution, or the like.

In a specific example, the method may include bioprinting the hydrogel composition prior to the dissolution of the hydrogel composition in an acidic solution. After dissolving a structure fabricated by bioprinting in the acidic solution, by measuring the content of phosphate released from the hydrogel composition, the calcium phosphate can be quantified.

In another specific example, the hydrogel composition may be a hydrogel bead composition. Likewise, the hydrogel bead composition contains a uniform content of calcium phosphate, and thus, by measuring the content of phosphate released from the hydrogel bead composition, the calcium phosphate can be quantified.

According to another aspect, provided is a cellular scaffold including: a biogel capable of three-dimensional co-culture of cells; and a calcium phosphate hydrogel composition.

The biogel includes an alginate and a gelatin, and the alginate and the gelatin may be each crosslinked. Further, the biogel is capable of three-dimensionally co-culturing cells.

In the present application, the term 'alginate' is used in its general meaning and includes algin, salts of alginic acid, derivatives of alginic acid, and alginic acid itself. The alginate may include calcium alginate, sodium alginate, potassium alginate, ammonium alginate, or magnesium alginate. In some specific examples, the alginate includes calcium, magnesium, and sodium salts of alginic acid, which can be obtained from the cell walls of brown algae. Some commercial types of alginate can be extracted from marine algae. Sodium alginate is a natural polyanionic copolymers extracted from brown algae and may include guluronic acid and mannuronic acid as its constituents. In some specific examples, calcium alginate, sodium alginate, potassium alginate, ammonium alginate, and magnesium alginate are water-soluble. Calcium chloride is stable, and in some cases, can be used to crosslink sodium alginate to form a water-insoluble material named calcium alginate. Alginate may be a copolymer of guluronate (G) and mannuronate (M) monomers. The G and M units are normally interconnected as GG, MM, and MG/GM blocks. The ratio, dispersion, and lengths of these blocks can determine chemical and physical characteristics of alginate molecules.

In the present application, the term "gelatin" may refer to a protein obtained by partial hydrolysis of collagen, the chief protein component in connective tissues in skin, bones, hides, etc. of the animal body. The gelatin may include gelatin derivatives as well as pure gelatin. For example, the chitosan derivatives may include at least one from phthalated chitosan, esterified chitosan, amidated chitosan, and formylated chitosan. With regard to the gelatin, its types (sources) are not particularly limited, and for example, gelatins derived from various sources including mammals and fish, e.g. beef bones, beef skins, pork bones, and pork skins, may be used. Further, the gelatin may be one having a molecular weight of 10,000 to 30,000.

The biogel may be one having dual-crosslinks. In a specific example, the dual-crosslinks may refer to the alginate and the gelatin being each crosslinked, and this is distinguished from crosslinking between alginate and gelatin. For example, the alginate may be immobilized by the crosslinked gelatin, and the gelatin may be immobilized by the crosslinked alginate. Further, without being limited to any particular theory, due to the dual-crosslinks where the alginate and the gelatin are each crosslinked, the biogel is able to remain in a gelled state at cell culture or cell differentiation temperatures. At typical cell culture temperatures, or cell differentiation temperatures which are temperatures causing one cells to differentiate to other cells, gelatins may form a sol and escape the biogel. Thus, in order to use typical gelatins as scaffolds, the use of toxic chemicals to increase its stability becomes necessary. On the contrary, in the biogel according to a specific example, the above-described double crosslink by two-step crosslinking, without the use of chemicals, allows the gelatin to remain substantially inside the biogel without dissolution at cell culture or cell differentiation temperatures. The gelatin substantially remaining inside the biogel may indicate that the biogel has a three-dimensional form to a degree that allows three-dimensional culturing of cells during cell culturing or cell differentiation. Accordingly, the crosslinks may be made by physical crosslinking, not by a chemical crosslinker. Further, the biogel according to a specific example may be one enhanced in its physical properties by the two-step crosslinking, even without using a chemical crosslinker.

In a specific example, the biogel may be one containing cells within. The cells may be cells or tissues to be cultured, or cells to be differentiated to other cells, inside the structure. In detail, the cells may be stem cells, osteoblasts, osteoclasts, or a combination thereof. The stem cells refer to cells having potency, and the cells having potency include, for example, blasts, hepatic stem cells, fibroblasts, myoblasts, adult stem cells, mesenchymal stem cells, adipose-derived mesenchymal stem cells, bone marrow-derived mesenchymal stem cells, neuron-derived mesenchymal stem cells, umbilical cord-derived mesenchymal stem cells, umbilical cord blood-derived mesenchymal stem cells, or a combination thereof.

In a specific example, the biogel containing the cells may be one cultured in media containing a growth factor, a differentiation factor, or a combination thereof. The growth factor may refer to a material capable of regulating growth and functions of the cells. The differentiation factor may refer to a material inducing cells to differentiate to tissues or to other cells. The growth factor or the differentiation factor may be, for example, M-CSF, FBS, IGF-1, IGF-2, TGF-$\beta$, FGFs, PDGF, PTHrP, BMPs, GDF, VEGF, RANKL, L-ascorbic acid 2-phosphate, dexamethasone, $\beta$-glycerophosphate, vitamin D, tauroursodeoxycholic acid, or a combination thereof. The biogel may be one cultured in the media over 3 days to 35 days. The biogel may be, for example, one cultured over 3 days to 5 days, 7 days to 10 days, 14 days to 21 days, or 28 days to 35 days. Here, when the culturing period is less than the above ranges, there may be issues where the culturing period is insufficient to achieve differentiation to osteoclasts, such that the cells would not perform bone resorption action or even if they do, only resorb an undetectably small amount of bone. When the culturing period exceeds the above ranges, there may be issues where the expression of osteoclast differentiation factor ceases to advance but decreases, and thus, during the culturing period, the cells would continue to proliferate, thus weakening the internal binding of the culture mass, and moreover, the properties of the culture mass whose shape is retained via ionic bonds would weaken from a long culturing period.

In a specific example, the cellular scaffold may be one having a structure in which a calcium phosphate hydrogel composition is imbedded in a biogel capable of three-dimensional co-culture.

The calcium phosphate hydrogel composition has a uniform content of phosphate, and thus, by measuring the content of phosphate contained in the hydrogel composition, a decrease amount of calcium phosphate can be quantitatively confirmed. The composition may be a three-dimensional gelled structure, which is included and integrally formed inside the biogel. Further, the composition may be prepared through: preparing a first composition by dissolving chitosan in a gelatin solution; preparing a second composition by mixing calcium phosphate with a calcium chloride solution; and adding the second composition to the first composition in a dropwise manner.

In a specific example, the chitosan may be included, with respect to 100 wt % of the first composition, in 0.1 wt % to 10 wt %, 0.1 wt % to 8 wt %, 0.1 wt % to 5 wt %, 0.1 wt % to 0.25 wt %, 0.25 wt % to 0.3 wt %, 0.15 wt % to 0.2 wt %, 1 wt % to 8 wt %, or 1 wt % to 5 wt %, and the calcium phosphate may be included, with respect to 100 wt % of the second composition, in 0.1 wt % to 10 wt %, 0.1 wt % to 8 wt %, 0.1 wt % to 5 wt %, 0.5 wt % to 6 wt %, 0.5 wt % to 3.5 wt %, 4.5 wt % to 7.5 wt %, or 1.5 wt % to 2.5 wt %.

In a specific example, the calcium phosphate may be included in 0.1 wt % to 10 wt % with respect to 100 wt % of the hydrogel composition. For example, the phosphate may be included in 0.1 wt % to 10 wt %, 0.1 wt % to 8 wt %, 0.1 wt % to 5 wt %, 0.5 wt % 8 wt %, 0.5 wt % to 5 wt %, 2.5 wt % to 5 wt %, or 1 wt % to 5 wt %.

According to another aspect of the present disclosure, provided is an in-vitro 3D osteoporosis model including the cellular scaffold. The osteoporosis model may be a model in which an environment exhibiting the characteristics of osteoporosis is created, and which serves as an experiment model alternative to the animal models. Details of the cellular scaffold are as described above.

According to another aspect of the present disclosure, provided is a method of predicting therapeutic effect on osteoporosis, the method including: injecting, in the osteoporosis model, a candidate compound for osteoporosis treatment; and quantifying phosphate inside a calcium phosphate hydrogel. Details of the osteoporosis model are as described above. The quantification of phosphate may include dissolving the hydrogel in an acidic solution; and measuring a content of phosphate released from the hydrogel.

In a specific example, the acidic solution may be a hydrogen chloride solution, a nitric acid solution, a sulfuric acid solution, an acetic acid solution, or the like.

In a method of preparing a hydrogel composition according to one aspect, by crosslinking a hydrogel through instantaneous adjustments of pH, the content of phosphate therein is made uniform, and thus, the calcium phosphate contained in the hydrogel composition can be quantitatively confirmed by measuring calcium salts or phosphates released from the calcium phosphate. Unlike typical compositions containing calcium phosphate compounds which necessitate high-temperature sintering and freeze-drying processes to enhance their properties, the method can prepare a biocompatible composition through room-temperature processes, and thus can be utilized in fabrication of osteoporosis tissues using a hydrogel composition that is chemically, physically similar to human bone tissues, and can be further utilized in an evaluation system for osteoporosis drugs using the hydrogel composition.

Further, an osteoporosis model according to another aspect allows three-dimensional co-culturing of osteoblasts and osteoclasts inside a biogel, and thus, the osteoporosis model can be prepared according to an intended use. Furthermore, as the model contains a calcium phosphate hydrogel having a uniform content of phosphate and thus enables quantification of calcium phosphate through measurement of a phosphate content, the model can screen candidate compounds for an osteoporosis drug and can effectively predict therapeutic effect of the drug on osteoporosis.

BRIEF DESCRIPTION OF DRAWINGS

FIG. 2A is a photograph of confirmation of calcium contained inside a hydrogel after staining the hydrogel with Alizarin Red S solution.

DETAILED DESCRIPTION

Hereinbelow, preferred examples are provided to assist in understanding of the present disclosure. However, the examples below are provided merely to assist in a better understanding of the present disclosure, and the scope of the present disclosure is not limited by the examples below.

EXAMPLES

Example 1. Preparation of Hydrogel Containing Chitosan and Calcium Phosphate 0.15 g of gelatin (Sigma, G2500) was placed in 8.5 ml of 0.1 M HCl and stirred at 120° C. at 120 rpm for 10-15 minutes.

Then, 0.15 g of chitosan (Sigma, 448869) was added and stirred in a water bath at 120° C. at 300 rpm for 3-4 hours, to produce a first mixture. Chitosan shows a high solubility in acidic environments of pH 6 or less, whereas it forms gel in environments of pH 6 or higher. Taking advantage of this unique feature, a mixture was prepared by using 0.1M HCl, which is a strong acid solvent of pH 1, as solvent for the first mixture. Next, 1.5 ml of 0.1 M HCl was placed in a 5 ml tube, and after adding 0.147 g of $CaCl_2$ (Wako, 031-00435) thereto, the tube was sufficiently vortexed.

Figure 1:
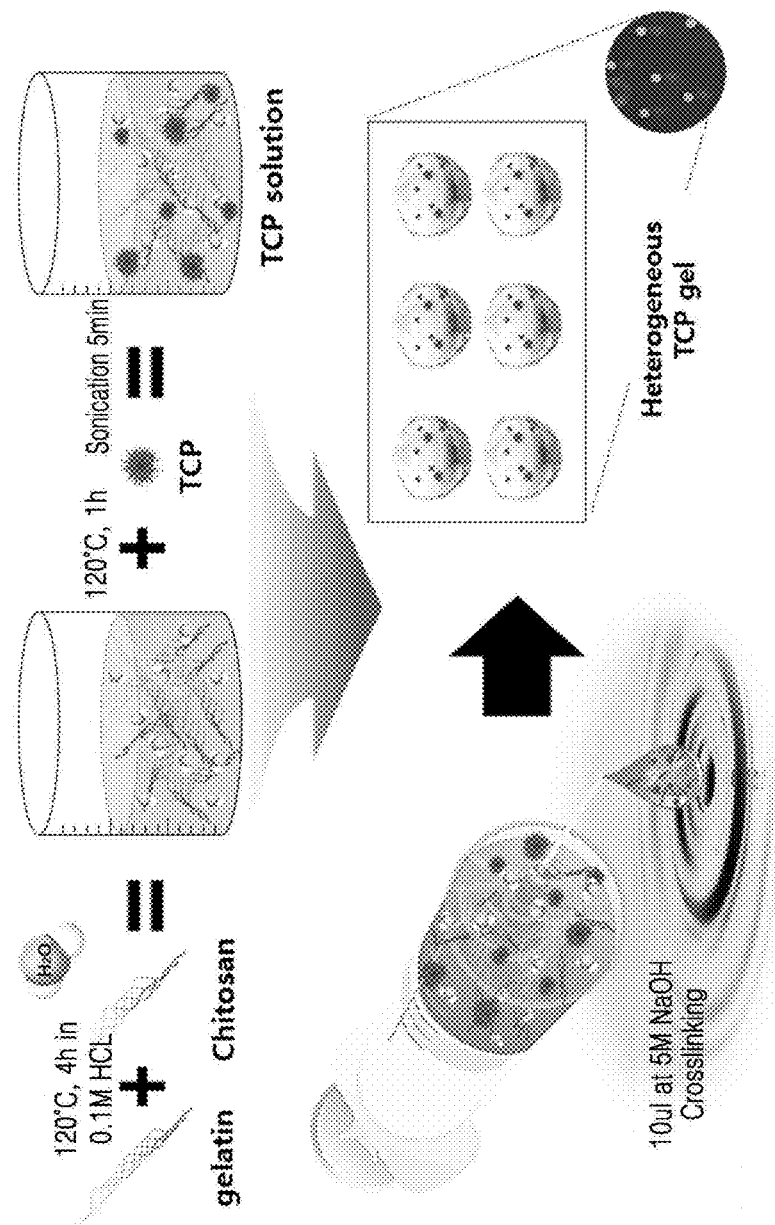
FIG. 1 illustrates a method of preparing a hydrogel composition and beads containing the composition, according to one aspect.

Then, 0.2 g of tricalcium phosphate (TCP) (Samchun, C0196) was added to the above solution and then sonicated for 10 minutes, to produce a second mixture. The second mixture was slowly added in a dropwise manner to the first mixture and stirred at 120° C. for 1 hour, to produce a hydrogel composition. Then, hydrogel beads were prepared by adding the composition in a dropwise manner, 10 µl at a time, to a 1 N NaOH solution, which is a strong alkaline aqueous solution, at room temperature. FIG. 1 illustrates a method of preparing a hydrogel composition according to one aspect and beads containing the composition.

In case of typical calcium phosphate compounds, their properties are enhanced through high-temperature sintering and freeze-drying processes. However, the above hydrogel composition is prepared by inducing crosslinking of calcium phosphate hydrogel through an instantaneous pH adjustment, taking advantage of the properties of chitosan that change in response to pH. In detail, when chitosan dissolved in a strong acid solution and the hydrogel composition having calcium phosphate uniformly dispersed therein are introduced into a strong alkaline solution, chitosan instantaneously entraps calcium phosphate in its surrounding to form a gel. Accordingly, it provides an advantage of being able to make adjustments such that the content of calcium phosphate contained the beads is uniform.

Example 2. Detection of Calcium Contained in Hydrogel Composition

Calcium phosphate-based materials have been extensively investigated for its chemical and physical similarities to human bone tissues. Of such calcium phosphates, TCP is composed of calcium and phosphoric acid, which are similar chemical components to those of natural bone, and releases calcium and phosphoric acid as it undergoes biodegradation.

Accordingly, calcium phosphate bound to calcium salts contained in the hydrogel was indirectly measured and thus quantified. To detect calcium contained in the hydrogel, a commonly known method, Alizarin Red S (ARS) assay was performed. First, the hydrogel composition prepared in Example 1 was 3D printed into two layers using a 26G needle, and after treatment with 1M NaOH for 5 minutes, was rinsed with D. W, to produce a hydrogel scaffold. Then, the scaffold was placed in 1% w/v ARS solution (pH 4.1-4.3) and incubated at room temperature. After removing the solution, the scaffold was rinsed with distilled water and then dried. Subsequently, using a digital camera, the stained scaffold was visualized. Thereafter, the scaffold stained with ARS was incubated in 10% w/v cetyl pyridinium chloride (CPC) in 10 mM sodium phosphate solution (pH 7) for 1 hour, to elute ARS. Subsequently, using a microplate reader, the absorbance of the eluent solution was measured at 562 nm. FIG. 2A is a photograph confirming calcium contained in a hydrogel after staining the hydrogel with ARS solution. As shown in FIG. 2A, it was found that when the amount of TCP contained in the hydrogel composition was varied from 0% to 5%, the staining intensity of the hydrogel was visually distinguishable in direct proportion to the amount of TCP.

Figure 2B:
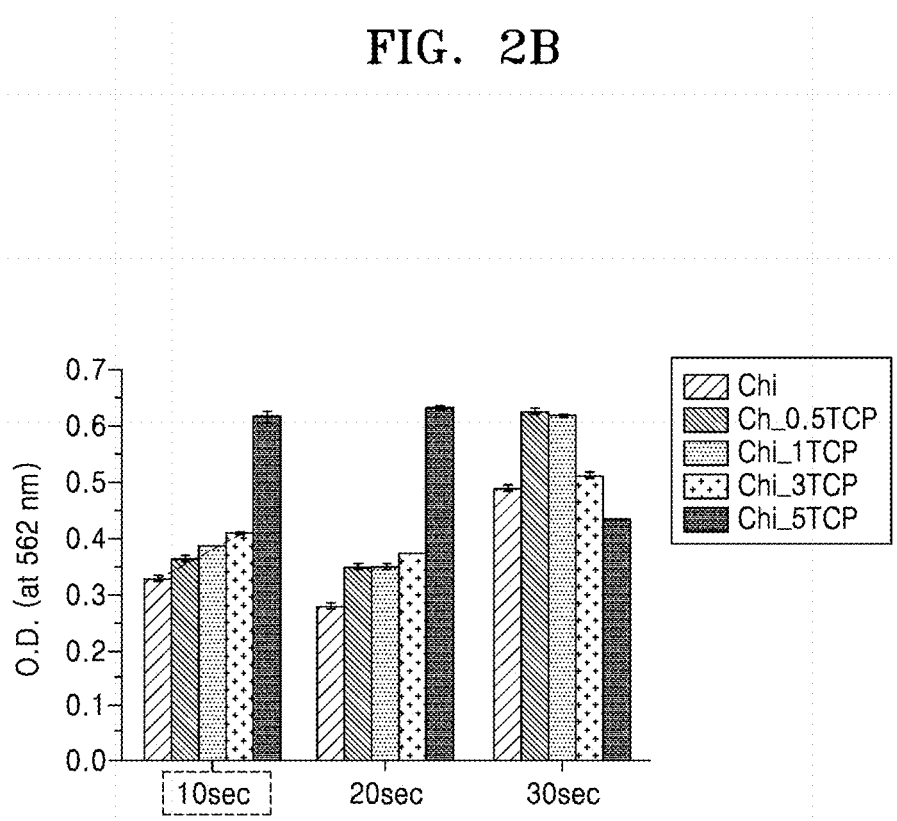
FIG. 2B is a graph of measurements of the amount of calcium contained in a hydrogel according to one aspect.

FIG. 2B is a graph of absorbances measured after eluting ARS bound to calcium salts in the amount of calcium contained in a hydrogel according to one aspect.

As shown in FIG. 2B, it was found that when the amount of TCP contained in the hydrogel composition was varied from 0% to 5% and the staining time was 10 seconds, the difference in absorbance value was directly proportional to the amount of TCP contained up to a TCP content of 3%.

Figure 2C:
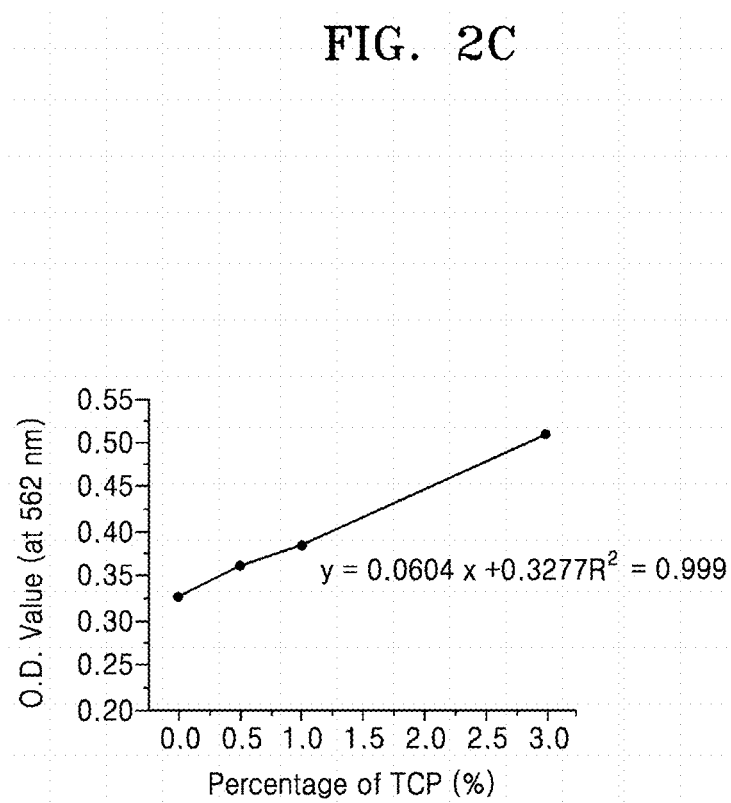
FIG. 2C is a graph for quantification of the amount of calcium contained in a hydrogel according to one aspect.

FIG. 2C is a graph for quantification of the amount of ARS eluted from a hydrogel according to one aspect.

As shown in FIG. 2C, it was found that up to a TCP content of 3% included in the hydrogel composition, the R-squared values were nearly 1 (0.99), revealing that the difference in absorbance value is directly proportional to the amount of TCP contained.

However, when the staining time was 10 seconds or more, difference in absorbance value could not be detected due to over-staining.

That is, calcium salts in the hydrogel composition according to one aspect can be quantified indirectly via ARS staining, which is a commonly used method of qualitative analysis of calcium.

Example 3. Detection of Phosphate Contained in Hydrogel Composition

Since TCP is composed of similar chemical components as natural bone, calcium and phosphoric acid, the TCP content can be measured through the measurement of released calcium salts or phosphates.

Accordingly, the measurement of TCP content was made through the measurement of phosphates released from TCP, using Malachite Green Phosphate Assay, which is based on the quantification of the green complex formed between Malachite Green, molybdate and free phosphates.

First, the hydrogel composition prepared in Example 1 was pretreated by rinsing with 37° C. D. W for 10 minutes for a total of three times. Then, the pre-treated hydrogel beads were transferred, one by one, to 1.5 ml tube, and after adding 1 ml of 1N HCl thereto, were dissolved at 60° C. to 70° C. over 1 hour.

Figure 3A:
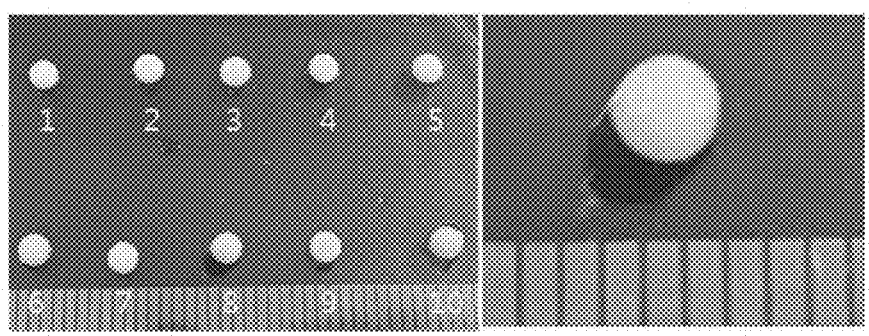
FIG. 3A is a photograph of a hydrogel composition according to one aspect, prepared as 3±0.5 mm size beads.
Figure 3B:
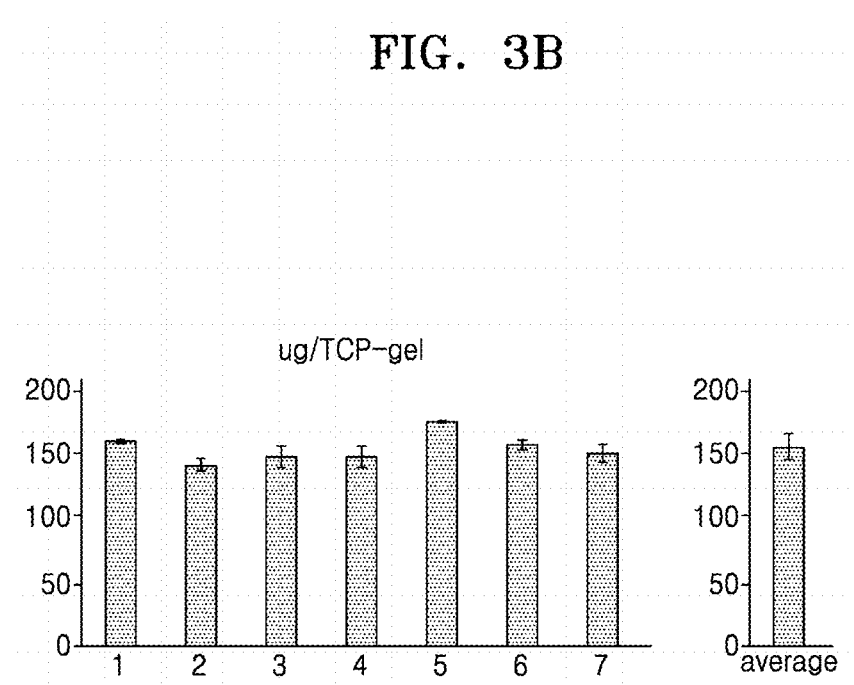
FIG. 3B is a graph of measurements of the content of phosphate included in hydrogel beads according to one aspect.

Thereafter, the solution in which the hydrogel beads were dissolved were diluted to 1/100 and loaded in 96 wells in an amount of 50 µl each, along with a standard solution (1-50 mM). Subsequently, 10 µl of Malachite Green Reagent A was added to each well and reacted for 10 minutes at room temperature, and then, 10 µl of Malachite Green Reagent B was further added to each well and reacted for 20 minutes at room temperature. Thereafter, the absorbance was measured at 620 nm. FIG. 3A is a photograph of a hydrogel composition according to one aspect, prepared as 3±0.5 mm size beads. FIG. 3B is a graph of measurements of TCP content in a hydrogel bead according to one aspect. As shown in FIG. 3A, when the hydrogel is prepared as beads, the beads have substantially the same size about 3 mm. Further, it was found that the TCP content inside the hydrogel beads was uniform at 100±15 µg/bead. (FIG. 3B). As such, it could be seen that the preparation method according to one aspect is able to produce hydrogel beads of a uniform size through instantaneous pH adjustments, and the content of phosphate contained in the hydrogel beads thus prepared is uniform.

Example 4. Detection of Ions Contained in Hydrogel Composition

Natural bone contains not only osteoblasts and osteoclasts, but also ions such as calcium ions and phosphate ions, and undergoes bone formation and bone resorption depending on the conditions.

Since TCP is composed of calcium and phosphoric acid, which are similar chemical components to those of natural bone, whether the hydrogel composition according to one aspect is realized as similar to natural bone was determined by measuring calcium ions or phosphate ions. In detail, 2 g (n=3) of the hydrogel composition prepared in Example 1 was eluted in 50 ml of 37° C. D. W at day 1, day 7, day 14, day 21, and day 28, and then, samples were collected with D. W changes. The collected samples were analyzed by confirming calcium and phosphate ion-release amounts in the unit of ppm (mg/L) using an inductively coupled plasma (ICP) spectrometer (ICP Spectrometer (I)).

Figure 3C:
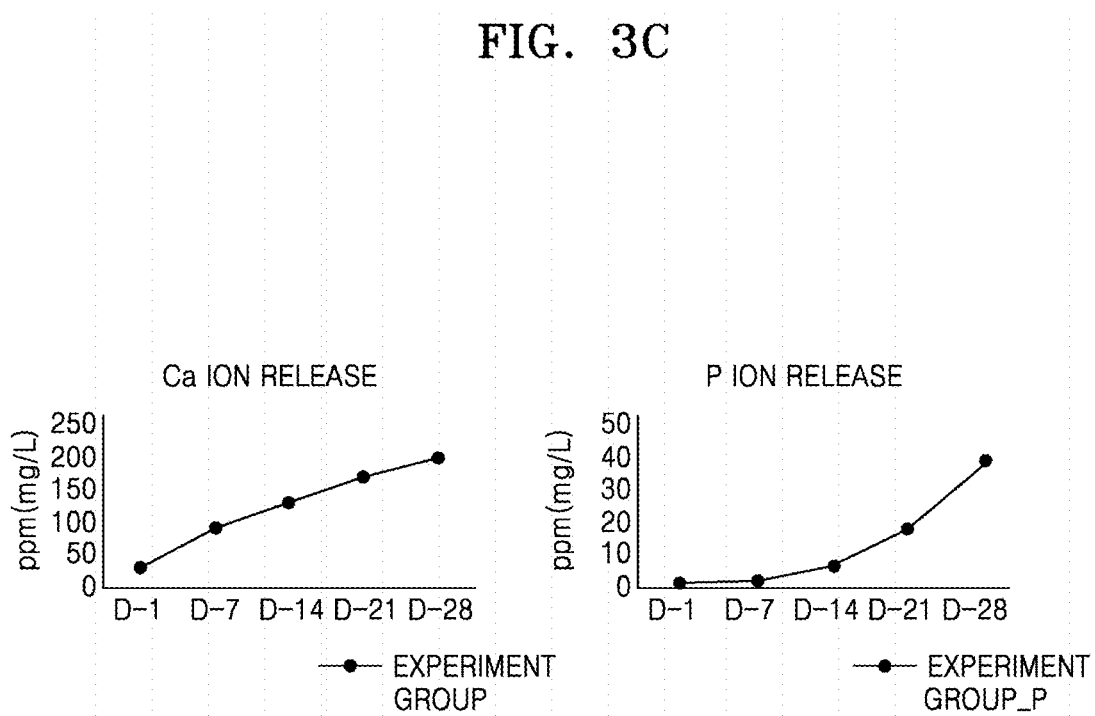
FIG. 3C is a graph of measurements of the contents of calcium ions and phosphate ions being released in hydrogel beads according to one aspect.

FIG. 3C is a graph of measurements of the amounts of calcium ions and phosphate ions released in hydrogel beads according to one aspect. As shown in FIG. 3C, it was found that when the hydrogel was prepared as beads, the amounts of calcium ions and phosphate ions released increased over time.

Since calcium ions and phosphate ions always exist around the cells in the human bone environment, the calcium ions and phosphate ions released overtime from the hydrogel according to one aspect may play a role in mimicking the bone environment in the surrounding cells. Accordingly, the hydrogel according to one aspect is expected to be able to mimic the in vivo environment even under an in-vitro environment.

Example 5. Characterization of Quantitative Analysis Method Through Detection of Phosphate Contained in Hydrogel Composition A method of quantitative analysis of the content of TCP through detection of phosphate contained in the hydrogel composition was characterized. In detail, hydrogel beads were prepared by adding TCP to the hydrogel composition prepared in Example 1 above, such that the content of TCP reaches 0%, 0.3%, 0.6%, and 1%. Then, the amounts of phosphate contained in the hydrogel beads were quantified by the same method as shown in Experimental Example 2 above.

Figure 4:
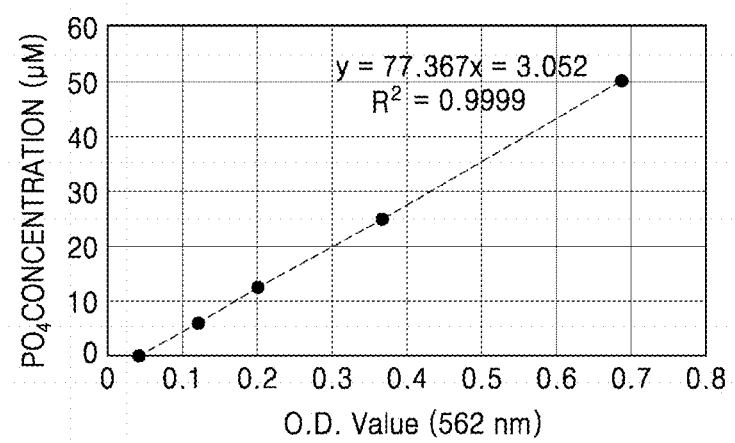
FIG. 4 is a standard curve graph of measurements, made using a phosphate standard solution, of the content of phosphate contained in hydrogel beads according to one aspect.

FIG. 4 is a standard curve graph of the content of phosphate contained in hydrogel beads according to one aspect, as measured using a phosphate standard solution.

Figure 5:
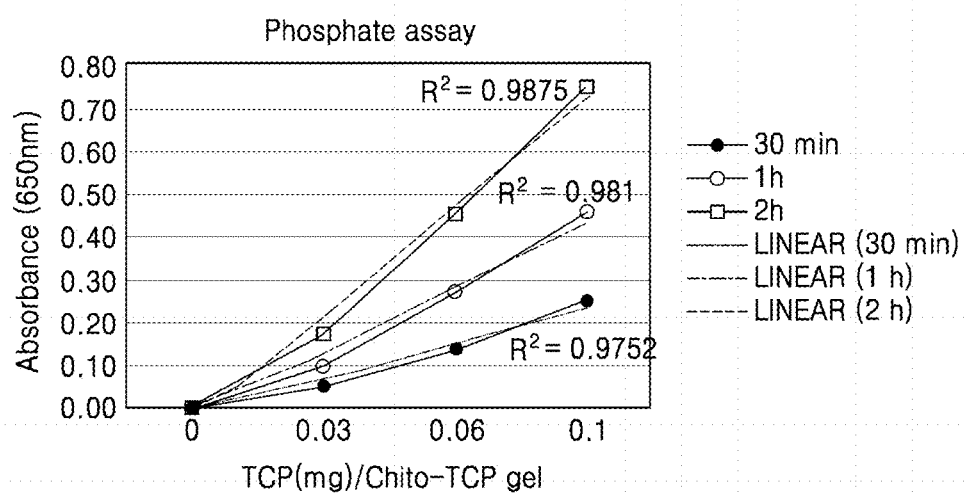
FIG. 5 is a graph of the content of phosphate contained in hydrogel beads according to one aspect, as a function of time.

In detail, after consecutively diluting 100 µM phosphate solution to 50 µM, 25 µM, 12.5 µM, and 6.25 µM, the absorbance of the solution was measured. Thereafter, a trend line was created using a series of measured values, and the R-squared value was calculated in order to determine a degree of proportionality. As a result, the R-squared value was revealed to be 0.9999, and thus, by applying the O. D value of the sample to the standard curve graph, the amount of PO4 dissolved therein can be accurately determined. FIG. 5 is a graph of the content of phosphate contained in hydrogel beads according to one aspect, as a function of time.

As shown in FIG. 5, a trend was observed that as the content of TCP contained in the hydrogel beads changes, the content of phosphate also changes in a manner directly proportional thereto ($R2>0.99$ or higher). That is, as the content of TCP in the hydrogel composition according to one aspect can be measured through quantification of calcium salts and phosphates, the hydrogel composition can be utilized as an evaluation system for assessment of osteoporosis tissues and confirming the efficacy of osteoporosis drugs.

Example 6. Preparation of BioGel Capable of 3D Co-Culture of Cells

To prepare a biogel capable of 3D co-culture, two-step crosslinking was performed. In detail, 3 g of gelatin (porcine skin type A, Sigma, USA) was placed in 100 ml of Dubecco's Phosphate-Buffered Saline (DPBS) (Welgene, Korea), and maintained at 60° C. on a magnetic stirrer hotplate until completely dissolved, to produce a gelatin solution.

Then, 2 g of alginate powder (Sigma, USA) was added to the gelatin solution prepared above and completely dissolved over 1 hour using a magnetic stirrer hotplate, to produce an alginate-gelatin mixture solution. The above mixture solution was then filtered using 0.2 µm syringe filter, and stored in a media bottle for later use. Next, the two-step crosslinking was performed. To perform the two-step crosslinking, the mixture solution was first subjected to gelation at 4° C. for 30 minutes to crosslink the gelatin, and then was mixed with 300 mM $CaCl_2$ solution and allowed to react at 4° C. for 30 minutes to crosslink the alginate. By performing the two-step crosslinking as described above, an alginate-gelatin mixture hydrogel was prepared.

Figure 6A:
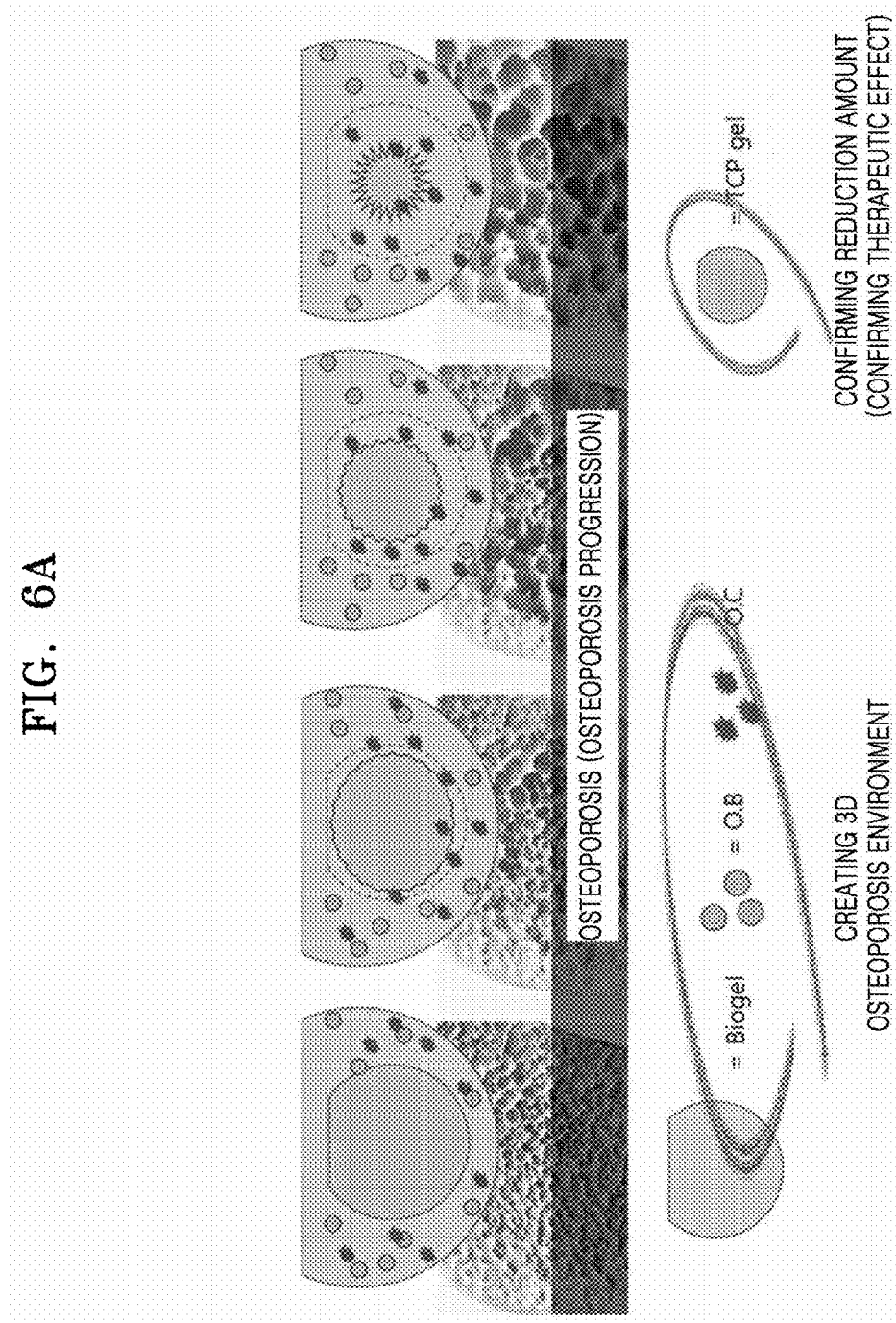
FIG. 6A is a schematic diagram of an osteoporosis model according to one aspect.
Figure 6B:
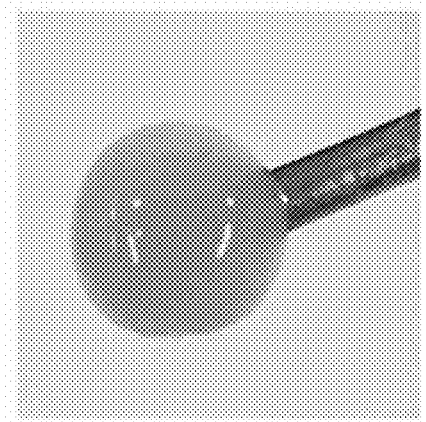
FIG. 6B is a photograph of a biogel prepared in a specific example, gelled in a three-dimensional form.
Figure 6C:
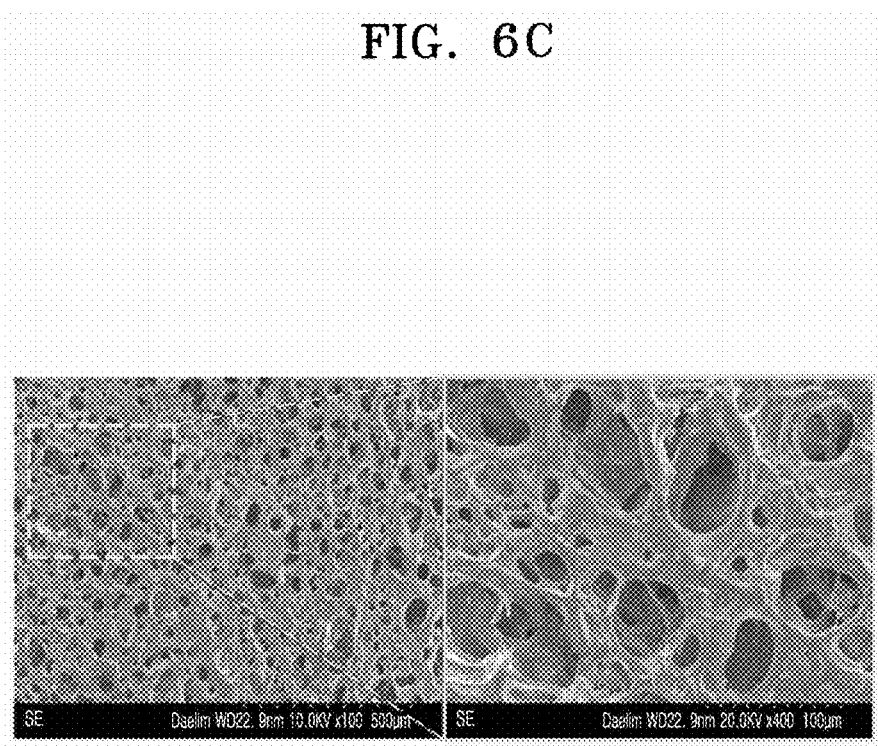
FIG. 6C is an SEM image of the inside of a biogel prepared in a specific example.

FIG. 6B is a photograph of a biogel prepared in a specific example, gelled in a three-dimensional form, and FIG. 6C is an SEM image of the inside of the biogel.

As shown in FIG. 6B and FIG. 6C, the biogel includes three-dimensional micropore shapes similar to the human microstructures. As such, it could be seen that the biogel has a structure that not only facilitates oxygen supply and circulation of nutrients, but also is advantageous for cell attachment, proliferation, and the like.

Example 7. Determination on Cytotoxicity of Biogel

To characterize the cytotoxicity test of the biogel prepared in Example 6, osteoblast progenitor cells, MC3TC-E1, and osteoclast progenitor cells, RAW264.7 were each three-dimensionally cultured. In detail, in the biogel, MC3TC-E1 and RAW264.7 were mixed with each other in an amount of $1\times10^6$ cells/ml and $5\times10^5$ cells/ml, and the biogel and 100 μL of the cell mixture solution were gelled using a casting gel. Then, the MC3TC-E1 culture mass and the RAW264.7 culture mass were each cultured in growth media supplemented with 100 U/ml of α-MEM (Welgene, Korea) and 100 μl/ml of streptomycin (Welgene, Korea).

Figure 7A:
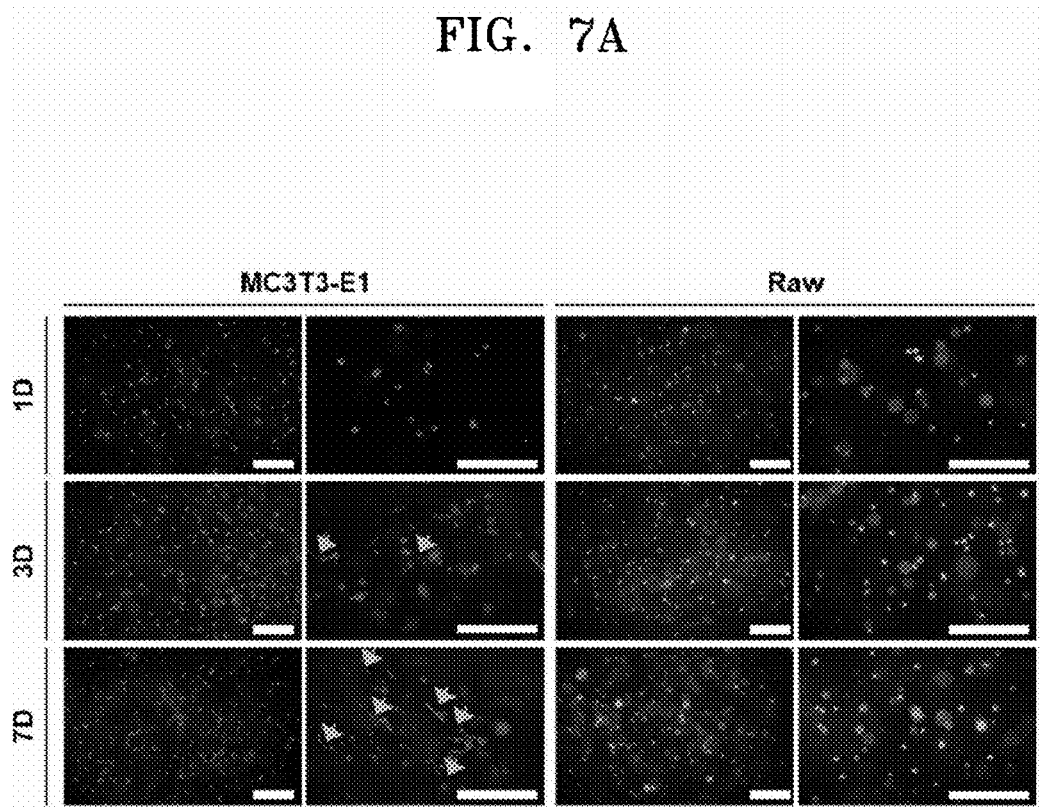
FIG. 7A is a fluorescence image confirming cytotoxicity of a biogel prepared in a specific example.
Figure 7B:
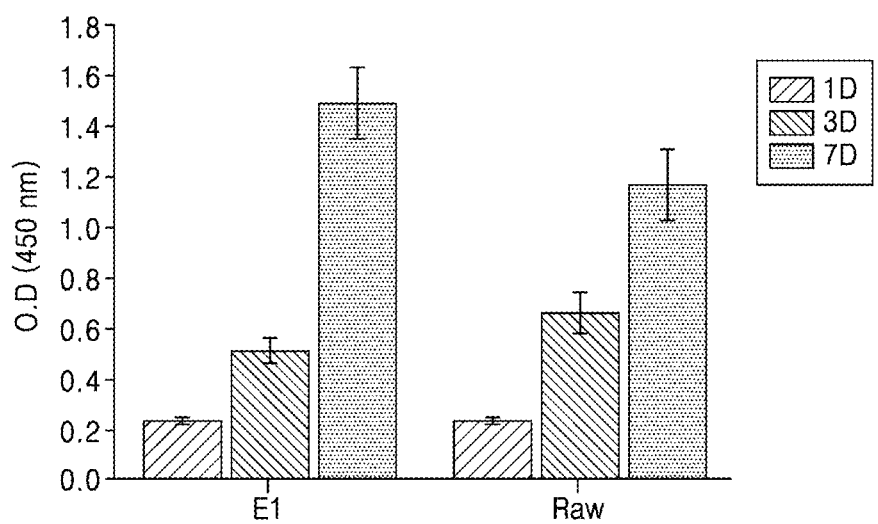
FIG. 7B is a graph confirming the cell viability of cells cultured in a biogel prepared in a specific example.

FIG. 7A is a fluorescence image showing the presence of cytotoxicity in a biogel prepared in a specific example. FIG. 7B is a graph showing the cell viability of cells cultured in a biogel prepared in a specific example. As shown in FIG. 7A, it was found that the amount of fluorescence, indicative of the cell proliferations of osteoblast progenitor cells MC3TC-E1, and osteoclast progenitor cells RAW264.7, increased over time. Further, in case of the MC3TC-E1 cells, as indicated by the arrows, fiber formation was observed from day 3 of culturing. That is, it could be confirmed that osteoblast progenitor cells could successfully attach and grow inside the biogel. Further, as shown in FIG. 7B, as a result of characterizing the cell proliferation more quantitatively using Cellrix Cell Viability assay kit, it was found that both MC3TC-E1 and RAW264.7 cells were successfully proliferating inside the biogel up to day 7 of culturing. Accordingly, it could be confirmed that the biogel according to one aspect has no cytotoxicity.

Example 8. Determination on Osteoblast-Osteoclast Composition Ratio Effective for Osteoporotic Environment 8-1. Culturing of Osteoblasts Osteoblasts progenitor cells, MC3TC-E1 were mixed with the biogel prepared in Example 6, in amounts of $7\times10^4$ ml and $1\times10^6$ ml, and 100 μL of each of the resulting mixture solution was gelled using a casting gel, to consequently yield three-dimensional culture mass, each containing $7\times10^3$ and $1\times10^5$ cells. Then, the three-dimensional culture mass were three-dimensionally cultured for 7 days in in osteoblast media, which were formed by adding 10 mM of β-glycerophosphate (Sigma Aldrich, USA), 50 μg/ml of ascorbic acid (Sigma Aldrich, USA), and 10 nM of dexamethasone (Sigma Aldrich, USA) to growth media supplemented with α-MEM (Welgene, Korea) supplemented with 10% fetal bovine serum (FBS) (Gibco, USA), 100 U/ml of penicillin (Welgene, Korea), and 100 μl/ml of streptomycin (Welgene, Korea). Thereafter, on day 3 and day 7 of culturing, differences in the expression level of ALP protein, which is an early osteoblast differentiation factor, were examined at different cell densities of culture mass, using ALP assay kit (Abcam, ab83369) and ALP staining kit (Sigma, P5869).

Figure 8A:
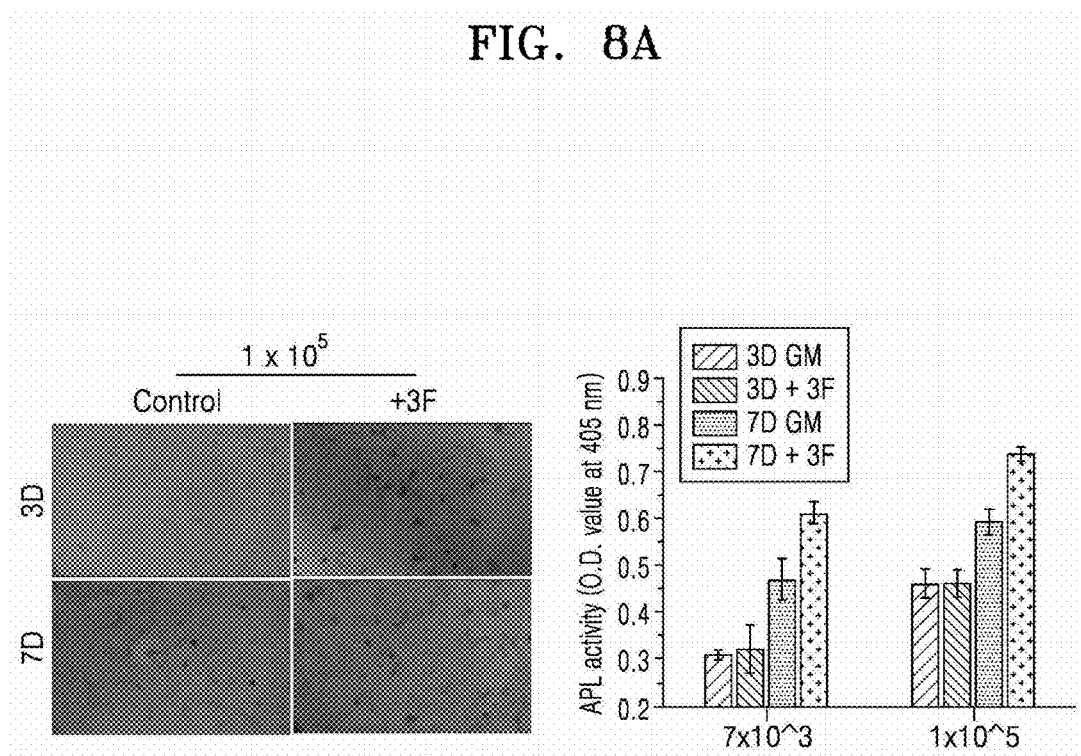
FIG. 8A shows photographs and a graph of differentiation profiles, confirmed by ALP staining and ALP assay, after culturing MC3T3-E1 cells in a biogel at different cell numbers, to determine a cell composition more effective for an osteoporotic environment.

FIG. 8A is photographs and a graph of differentiation profiles, confirmed by ALP staining and ALP assay, after culturing MC3T3-E1 cells and RAW264.7 cells in a biogel at different cell numbers, to determine a cell composition ratio more effective for the osteoporotic environment. As shown in FIG. 8A, it was found that during the culturing period, the expression of osteoblast differentiation factor, ALP, was increased in the growth factor-containing experimental group (+3F), compared to the control group (GM) cultured in growth media, and a further higher level of ALP was expressed on day 7 of culturing.

Further, it was found that the ALP expression level was higher when the number of cells contained in culture mass was $1\times10^6$ than when it was $7\times10^3$.

Accordingly, it could be seen that the cell number of osteoblast progenitor cells MC3T3-E1 that is optimal for preparing an osteoporosis model was $1\times10^6$.

Figure 8B:
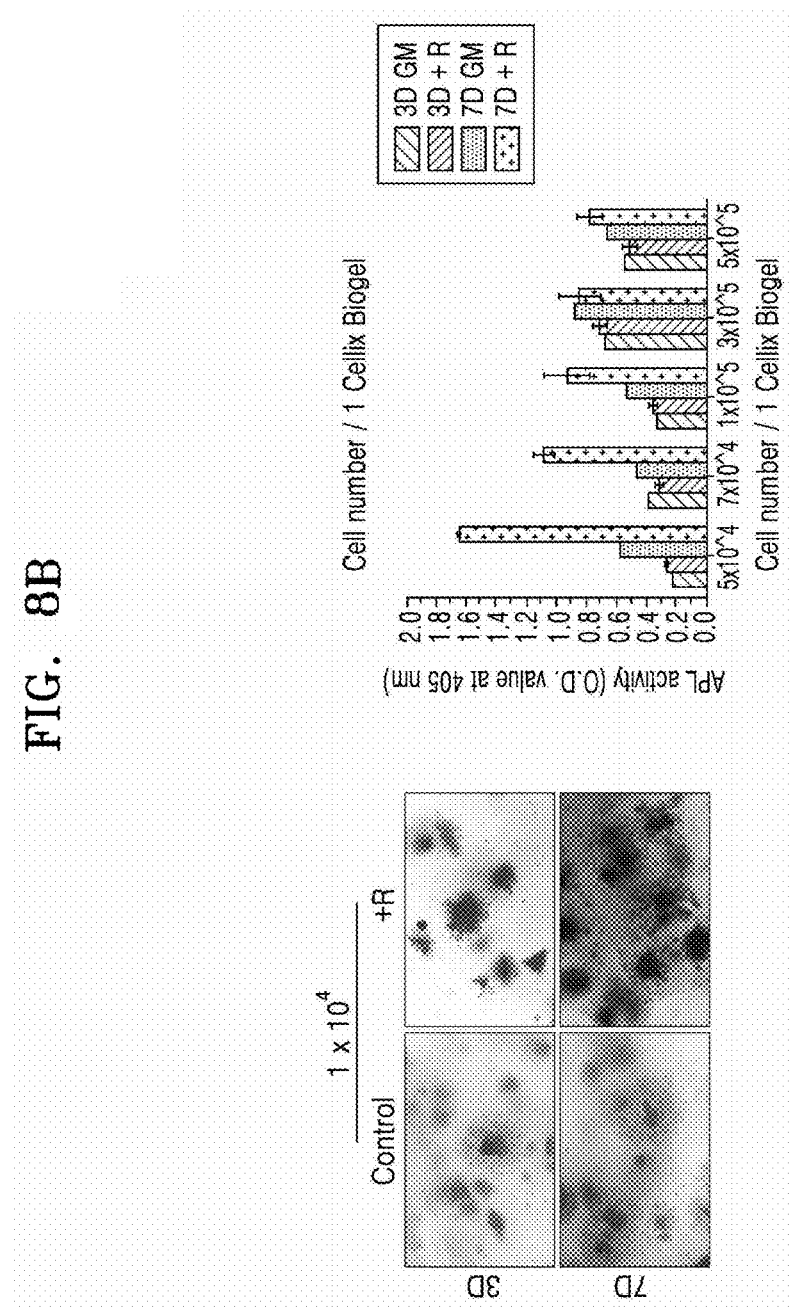
FIG. 8B shows photographs and a graph of differentiation profiles, confirmed by TRAP staining and ACP assay, after culturing RAW264.7 cells in a biogel at different cell numbers, to determine a cell composition more effective for an osteoporotic environment.

8-2. Culturing of Osteoclasts Osteoclast progenitor cells RAW264.7 were mixed with the biogel prepared in Example 6, in amounts of $5\times10^5$ cells/ml, $7\times10^5$ cells/ml, $1\times10^6$ cells/ml, and $3\times10^6$ cells/ml, and 100 μL of each of the resulting mixture liquids was gelled using a casting gel, to consequently yield three-dimensional culture mass, each containing $5\times10^4$ cells, $7\times10^4$ cells, $1\times10^5$ cells, $3\times10^5$ cells, and $5\times10^5$ cells. Then, the three-dimensional culture mass were three-dimensionally cultured for 7 days in osteoclast media, which were formed by adding 100 ng/ml of Rankl to growth media containing α-MEM (Welgene, Korea) supplemented with 10% fetal bovine serum (FBS) (Gibco, USA), 100 U/ml of penicillin (Welgene, Korea), and 100 μl/ml of streptomycin (Welgene, Korea). Then, using ACP assay kit (Abcam, ab83367) and TRAP staining kit (Sigma, 181A), differences in the expression level of osteoclast differentiation factor were examined at different cell numbers. FIG. 8B is photographs and a graph of differentiation profiles, confirmed by TRAP staining and ACP assay, after culturing RAW264.7 cells in the biogel at different cell numbers, to determine a cell composition ratio more effective for the osteoporotic environment. As shown in FIG. 8B, during the culturing period, it was found that the expression of osteoclast differentiation factor ACP was increased in the growth factor-containing experimental group (+R), compared to the control group (GM) cultured in growth media, and a further higher level of ACP was expressed on day 7 of culturing.

Further, it could be confirmed that the ACP expression was highest when the number of cells contained in culture was $5\times10^4$, and as the number of cells increased, the expression level of ACP was decreased. That is, it could be confirmed that the cell number of osteoclast progenitor cells RAW264.7 optimal for preparing the osteoporosis model is $5\times10^4$.

8-3. Determination on whether osteoblasts and osteoclasts influence each other's differentiation It was determined whether osteoblasts and osteoclasts influence each other's differentiation.

In detail, three-dimensional culture mass were prepared using $1\times10^6$ cells/ml of osteoblast progenitor cells MC3TC-E1, and $5\times10^5$ cells/ml of osteoclast progenitor cells RAW264.7, in the biogel prepared in Example 6 above. The RAW264.7 culture mass was treated with an osteoblast differentiation induction factor (+3F) and the MC3T3-E1 culture mass was treated with an osteoclast differentiation induction factor (+R).

Subsequently, on day 3 and day 7 of culturing, the MC3T3-E1 cells were measured for the osteoclast differentiation marker ACP, and the RAW264.7 cells were measured for the osteoblast differentiation marker ALP, to determine the influence of their respective differentiation markers on each other.

Figure 9A:
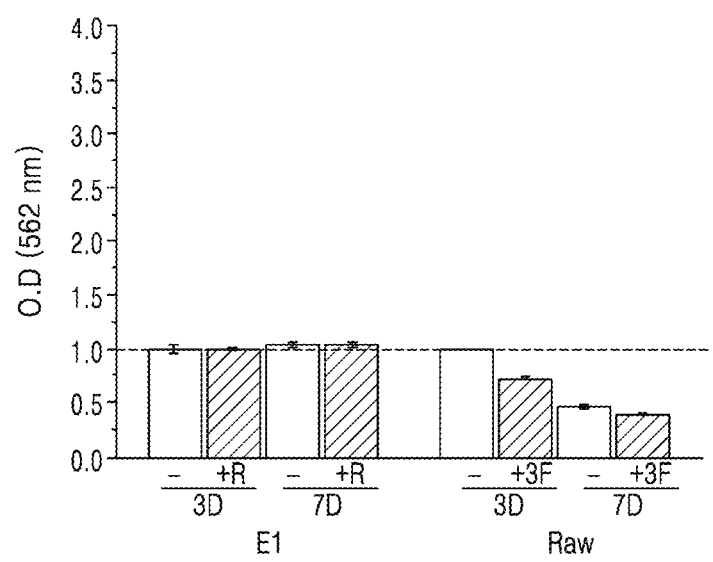
FIG. 9A is a graph showing an interaction effect of osteoblast and/or osteoclast induction media on RAW264.7 cells and/or MC3T3-E1 cells, confirmed by ALP assay.
Figure 9B:
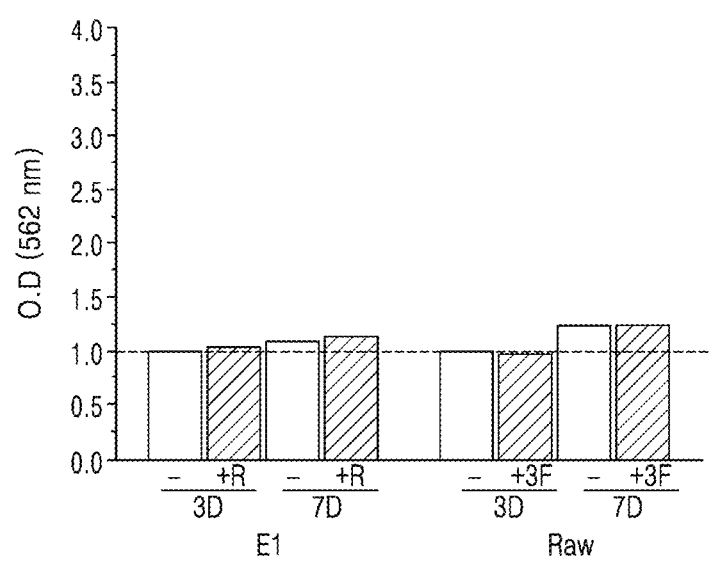
FIG. 9B is a graph showing an interaction effect of osteoblast and/or osteoclast induction media on RAW264.7 cells and/or MC3T3-E1 cells, confirmed by ACP assay.

FIG. 9A is a graph showing an interaction effect of the osteoblast and/or osteoclast induction factors on the RAW264.7 and/or MC3T3-E1 cells, confirmed by ALP assay. FIG. 9B is a graph showing an interaction effect of the osteoblast and/or osteoclast induction factors on the RAW264.7 and/or MC3T3-E1 cells, confirmed by ACP assay. As shown in FIG. 9A, it was found that in the osteoblast progenitor cells MC3T3-E1, when treated with the osteoclast differentiation induction factor, there was little expression of the osteoblast differentiation marker ALP induced, and even in the osteoclast progenitor cells RAW264.7 treated with the osteoblast differentiation induction factor, it was found that there was little expression of the osteoblast differentiation marker ALP induced.

Also as shown in FIG. 9B, it was found that in the osteoblast progenitor cells MC3T3-E1, when treated with the osteoclast differentiation induction factor, there was little expression of the osteoclast differentiation marker ACP induced, and even in the osteoclast progenitor cells RAW264.7 treated with the osteoblast differentiation induction factor, it was found that there was little expression of the osteoclast differentiation marker ACP induced. That is, it could be confirmed that osteoblasts and osteoclasts were rarely influenced by each other's differentiation induction factors.

Example 9. Creation of Osteoporotic Environment Through Co-Culture of Cells in Biogel 9-1. Creating the Bone Formation Environment Through Co-Culture of Osteoblasts and Osteoclasts First, a casting gel mold was prepared for gelation of the biogel.

In detail, after dissolving 0.5% agarose in 300 mM CaCl2 solution, the Phenol Red solution was added in an amount of 5 mg/L to produce a casting gel solution. Then, after introducing 5-5.5 ml of the casting gel solution into a casting tray, a three-dimensional semi-spherical casting mold was inserted in the casting tray, and after completely solidifying the casting gel solution, the casting mold was carefully removed to produce a three-dimensional semi-spherical casting gel mold. The biogel, $1\times10^5$ cells/ml of osteoblast progenitor cells MC3T3-E1, and $5\times10^4$ cells/ml of osteoclast progenitor cells RAW264.7, were introduced into the casting gel mold and subjected to gelation to yield a three-dimensional co-culture mass. Then, the co-culture mass was cultured in the following media: media treated only with an osteoblast differentiation induction factor (+3F); media only treated with an osteoclast differentiation induction factor (+R); and media treated with both osteoblast differentiation induction factor and osteoclast differentiation induction factor (+3F+R). Then, osteoblast differentiation profiles were characterized through ALP expression levels.

Figure 10A:
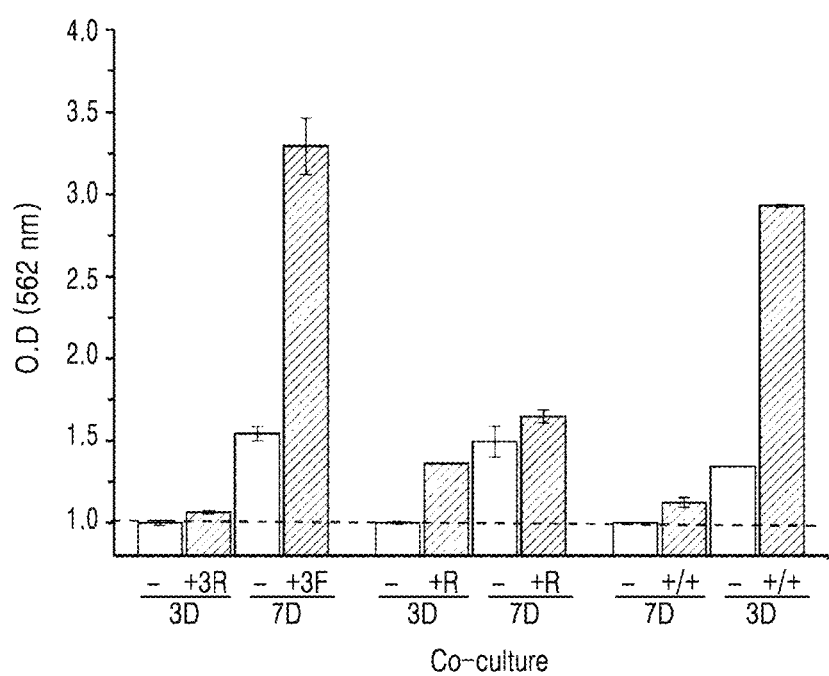
FIG. 10A is a graph of differentiation profiles, confirmed by ALP assay, after co-culturing MC3T3-E1 cells and RAW264.7 cells in a biogel to create a bone formation environment through co-culture of osteoblast progenitor cells and osteoclast progenitor cells.
Figure 10B:
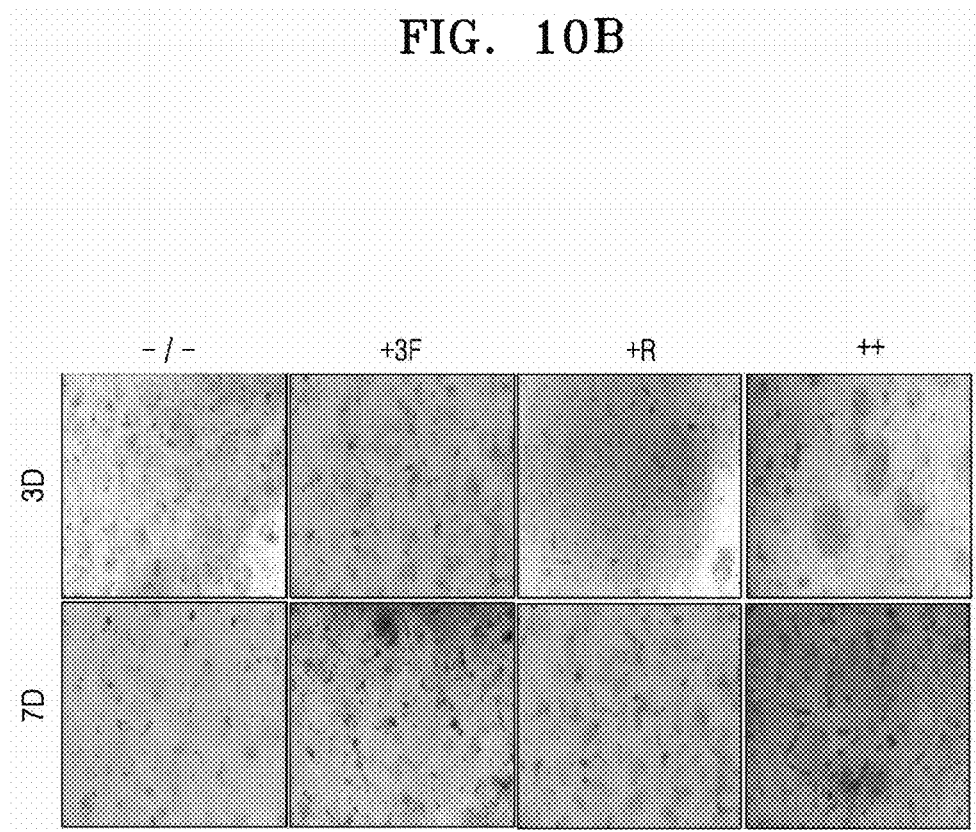
FIG. 10B is a graph of differentiation profiles, confirmed by ALP staining, after co-culturing MC3T3-E1 cells and RAW264.7 cells in a biogel to create a bone formation environment through co-culture of osteoblast progenitor cells and osteoclast progenitor cells.

FIG. 10A is a graph of differentiation profiles, confirmed by ALP assay, after co-culturing MC3T3-E1 cells and RAW264.7 cells in the biogel culture mass to create a bone tissue environment through co-culture of osteoblasts and osteoclasts, and FIG. 10B is a photograph of differentiation profiles confirmed by ALP staining. As shown in FIG. 10A and FIG. 10B, it was found that when treated only with the osteoblast differentiation induction factor, the ALP expression was increased as the MC3T3-E1 cells differentiated to osteoblasts, and when treated only with the osteoclast differentiation induction factor, there was a trace amount of ALP expressed.

This indicates that it was likely that as the osteoclast progenitor cells RAW264.7 differentiated to osteoclasts, the osteoblast progenitor cells MC3T3-E1 reacted so as to maintain homeostasis. Further, when treated with both osteoblast differentiation induction factor and osteoclast differentiation induction factor, the ALP expression level was slightly lower than when treated only with the osteoblast differentiation induction factor. This result is likely due to an influence from the osteoclast progenitor cells RAW264.7 as they differentiate to osteoclasts, and is also a response that can be likened to the interactions between osteoblasts and osteoclasts taking place in the actual in vivo environment to maintain homeostasis. 9-2. Creating the bone resorption environment through co-culture of osteoblasts and osteoclasts Under the same conditions as shown in Example 9-1, osteoclast differentiation profiles were characterized by ALP expression levels.

Figure 11A:
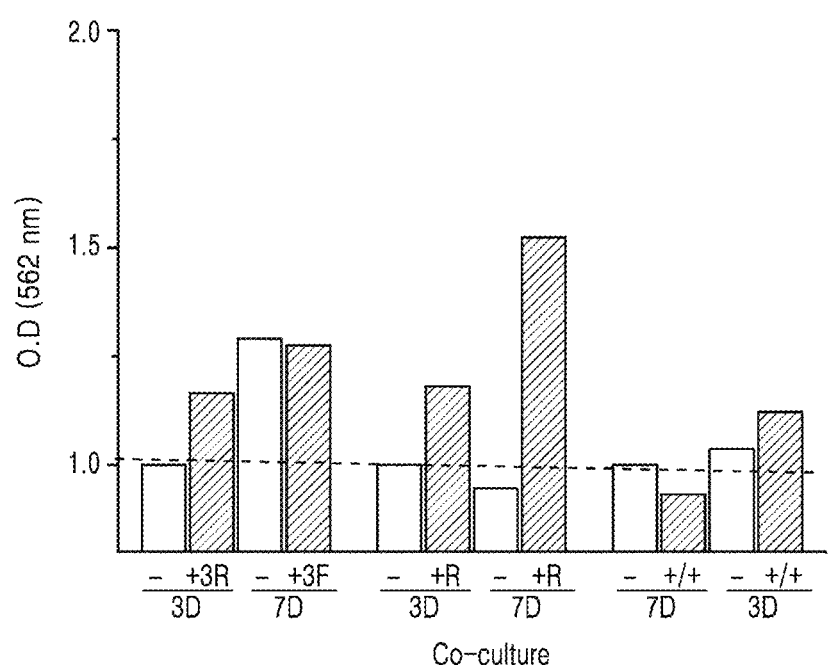
FIG. 11A is a graph of differentiation profiles, confirmed by ACP assay, after co-culturing MC3T3-E1 cells and RAW264.7 cells in a biogel to create a bone resorption environment through co-culture of osteoblast progenitor cells and osteoclast progenitor cells.
Figure 11B:
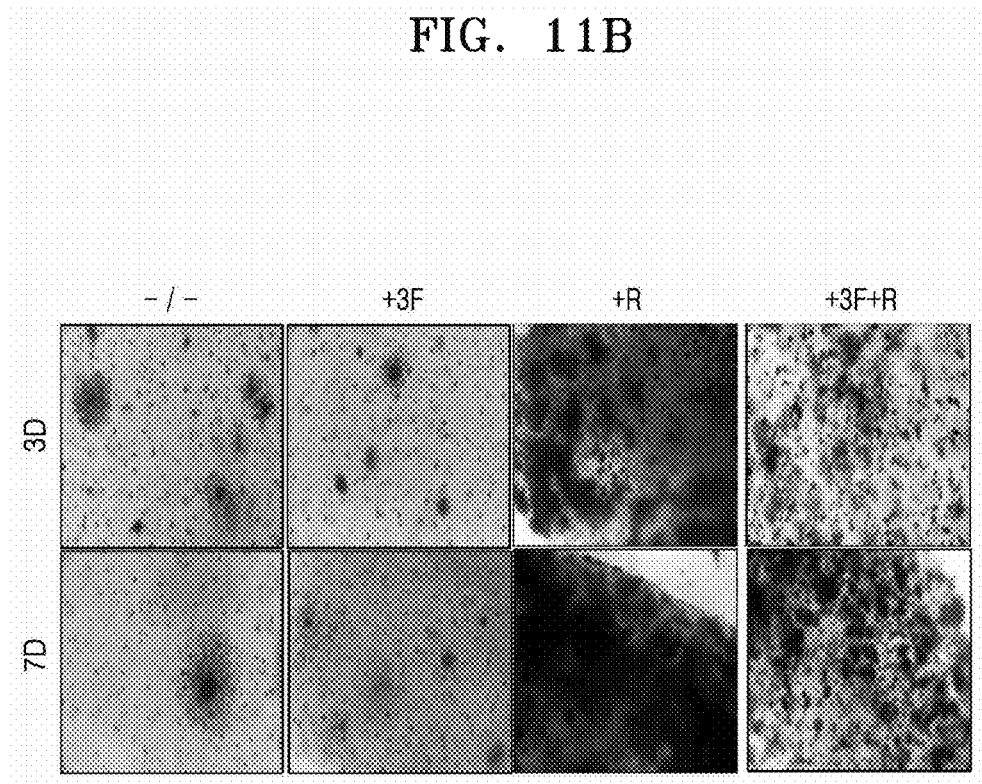
FIG. 11B is a graph of differentiation profiles, confirmed by TRAP staining, after co-culturing MC3T3-E1 cells and RAW264.7 cells in a biogel to create a bone resorption environment through co-culture of osteoblast progenitor cells and osteoclast progenitor cells.

FIG. 11A is a graph of differentiation profiles, confirmed by ACP assay, after co-culturing MC3T3-E1 cells and RAW264.7 cells in a biogel culture mass to create the bone resorption environment through co-culture of osteoblasts and osteoclasts, and FIG. 11B is a photograph of the differentiation profiles confirmed by TRAP staining.

As shown in FIG. 11A and FIG. 11B, it was found that when treated only with the osteoblast differentiation induction factor, there was little induction for differentiation to osteoclasts in both MC3T3-E1 cells and the RAW264.7 cells, and this result is likely to indicate that as the MC3T3-E1 cells were differentiating to osteoblasts, some of the RAW264.7 cells reacted so as to maintain homeostasis, thus giving rise to an early ACP expression.

Further, it was found that when treated only with the osteoclast differentiation induction factor, the ACP expression level was increased as the RAW264.7 were differentiated to osteoclasts, and the expression level was higher on day 7 of culturing compared to day 3. Further, the treatment with both osteoblast differentiation induction factor and osteoclast differentiation induction factor resulted in a lower ACP expression level than when treated only with the osteoclast differentiation induction factor. This result is likely due to an influence from the osteoblast progenitor cells MC3T3-E1 as they differentiate to osteoblasts, and is a response that can be likened to the interactions between osteoblasts and osteoclasts taking place in the actual in-vivo environment to maintain homeostasis.

9-3. Creating the osteoporotic environment through co-culture of mesenchymal stem cells and hematopoietic stem cells In the casting gel mold prepared in Example 9-1, 40 μl of a mixed solution prepared by mixing the biogel with $6\times10^6$ cells/ml of HSCs, and $0.5\times10^6$ cells/ml, $1\times10^6$ cells/ml, or $1.5\times10^6$ cells/ml of MSCs, were gelled to form co-culture mass.

Subsequently, the co-culture mass were cultured in MCSF-treated culture media for 5 days to induce a primary differentiation to macrophages, and then were additionally cultured for 5 days in media containing both MCSF and osteoclast differentiation induction factor (co-cultured in M+R). In addition, the co-culture mass was cultured for 2 days in media containing both MSCF and the osteoclast differentiation induction factor, and then was additionally cultured for 3 days in media further containing an osteoblast differentiation induction factor (co-cultured in M+R+3Fs).

Figure 12:
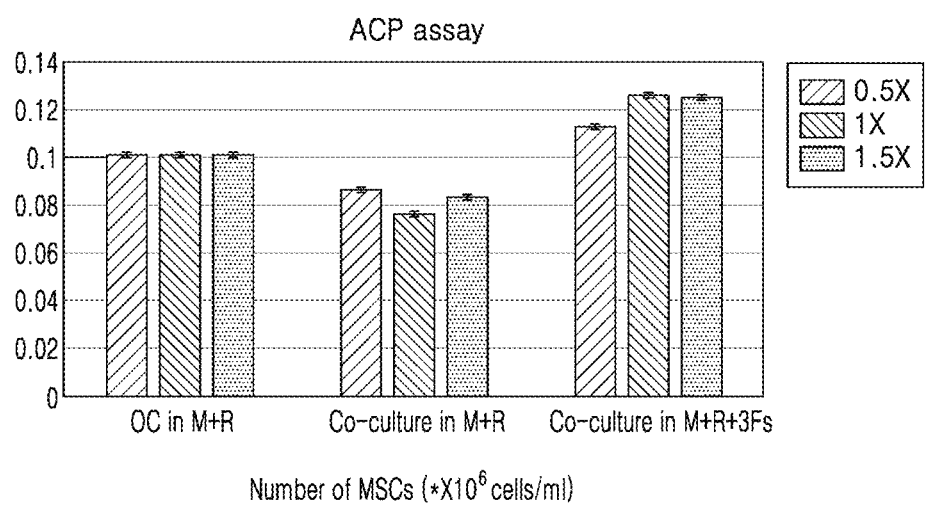
FIG. 12 is a graph of differentiation profiles, confirmed by ACP assay, after co-culturing MSCs and HSCs in a biogel to create an osteoporotic environment through co-culture of mesenchymal stem cells and hematopoietic stem cells.

A culture mass containing $6\times10^6$ cells/ml of HSCs in 40 μl of biogel was cultured in MCSF-containing media for 5 days, and was additionally cultured for 5 days in media containing both MCSF and osteoclast differentiation induction factor. FIG. 12 is a graph of differentiation profiles confirmed by ACP assay, after co-culturing mesenchymal stem cells (MSCs) and hematopoietic stem cells (HSCs) in the biogel to create the osteoporotic environment through co-culture of MSCs and HSCs. A shown in FIG. 12, when analyzed with reference to the ACP expression level of the control group, the co-culture mass of MSCs and HSCs, when cultured under osteoclast differentiation induction condition (M+R), exhibited a lower ACP expression compared to the control group. Meanwhile, the co-culture mass, when treated with both osteoblast and osteoclast differentiation induction factors (M+R+3Fs), exhibited a higher ACP expression compared to the control group.

Therefore, it could be confirmed that the cell numbers of HSCs and MSCs optimal for inducing the osteoporotic environment are $6\times10^6$ cells/ml and $1\times10^6$ cells/ml, respectively.

Example 10. Preparation of TCP Hydrogel Composition 0.15 g of gelatin (Sigma, G2500) was added in 8.5 ml of 0.1 M HCl and stirred at 120° C. at 120 rpm for 10-15 minutes. Then, after adding 0.15 g of chitosan (Sigma, 448869), the resulting mixture was heated and stirred in a water bath at 120° C. at 300 rpm for 3-4 hours, to produce a first mixture.

Here, the rpm rate was adjusted so as to ensure a thorough mixing of slurry, and when needed to be left overnight, the stirrer was adjusted to 60° C. and 80 rpm. Subsequently, 1.5 ml of 0.1 M HCl was placed in a 5 ml tube, and after adding 0.147 g of $CaCl_2$ (Wako, 031-00435) thereto, the tube was sufficiently vortexed.

Then, 2 g of TCP (Samchun, C0196) was added to the resulting solution and then sonicated for 10 minutes, to produce a second mixture. The second mixture was slowly added to the first mixture in a dropwise manner using 200p tip, and the resulting mixture was stirred at 120° C. over 1 hour.

Then, the resulting mixture was added in a dropwise manner, 10 μl at a time, to prepare a TCP hydrogel composition.

Example 11. Preparation of Biogel and TCP Hydrogel Structure

A cellular structure was prepared using the biogel prepared in Example 6 and the TCP hydrogel prepared in Example 10. First, 5.5 ml of a casting gel solution was introduced into the casting gel mold prepared in Example 9-1 and was completely solidified at 4° C. Then, 40 μl of a mixture, prepared by mixing MSCs and HSCs with the biogel, was added to the casting mold and was subject to gelation such that the TCP hydrogel was positioned in the middle of the biogel. Then, the gelled biogel-TCP structure was placed in a plate containing culture media and was incubated at 37° C.

Example 12. Creating Osteoporotic Environment Through Co-Culture of Osteoblasts and Osteoclasts in Biogel and TCP Hydrogel Scaffold Using the composite composition prepared in Example 11, osteoblasts and osteoclasts were co-cultured under the conditions described in Example 9-3 to create the osteoporotic environment.

Figure 13A:
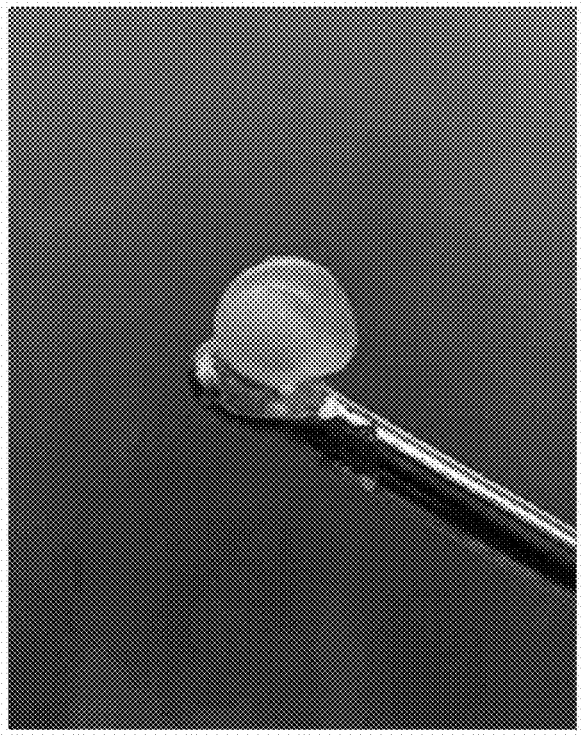
FIG. 13A is a photograph of a cellular structure in which a biogel prepared in Example 1 is combined with a TCP hydrogel prepared in Example 5.
Figure 13B:
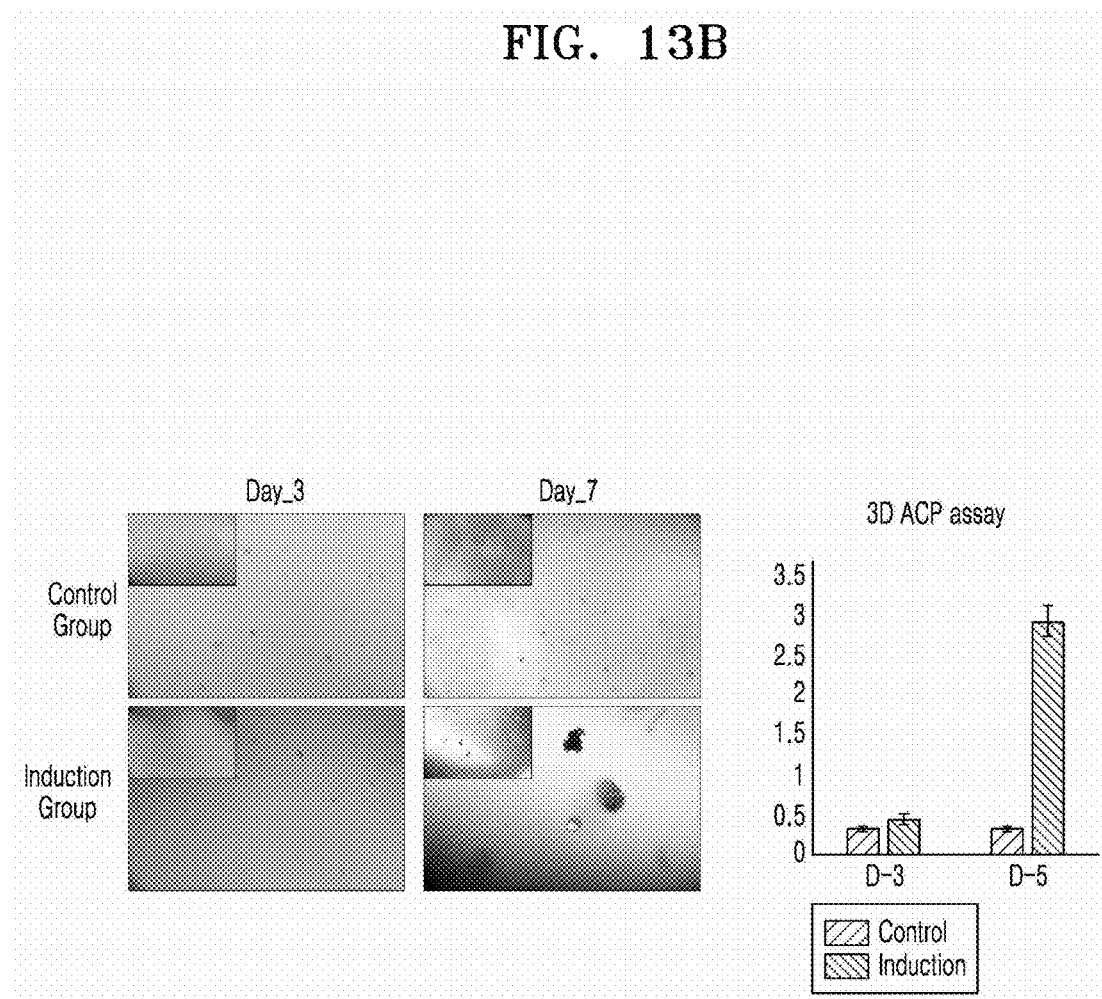
FIG. 13B is a result of confirming the differentiation of osteoclasts by performing TRAP staining and an ACP assay, after culturing a cellular structure in which a biogel is combined with a TCP hydrogel in normal culture media and induction media, separately.

Then, to confirm the osteoclast differentiation factor of RAW264.7 contained in a concentration of $1\times10^6$/ml (Biogel) in culture mass, the control group and the experimental group were each cultured using normal culture media and induction media, respectively, and samples were collected on day 3 and day 5 to characterize the differentiation profiles using TRAP staining and ACP assay. FIG. 13A is a photograph of a cellular structure in which a mixture of the biogel prepared in Example 6 and the TCP hydrogel prepared in Example 10 are combined. As shown in FIG. 13A, it could be seen that a hydrogel scaffold according to one aspect has a structure in which the TCP hydrogel is embedded in the biogel. FIG. 13B is a result of confirming the differentiation of osteoclasts by performing TRAP staining and ACP assay, after culturing a cellular structure in which a biogel is combined with a TCP hydrogel, in normal culture media and induction media, respectively.

As shown in FIG. 13B, on day 3, there was little difference between the normal culture media and the induction media in terms of the degree of differentiation of osteoclasts.

However, on day 7, it was found that osteoclast differentiation markers in the cellular structure cultured in the induction media were significantly higher than those in the cellular structure cultured in the normal culture media. That is, the cellular structure according to one aspect can mimic the osteoclast differentiation environment, and thus can create the osteoporotic environment.

Example 13. Characterization of Osteogenic Differentiation Potential of Biogel and TCP Hydrogel Composite Composition The osteogenic differentiation potential of the composite composition prepared in Example 11 was confirmed by ALP staining of TCP beads. In detail, $4\times10^3$ MC3T3-E1 cells were seeded per well in a 24-well plate and cultured for 7 days with a single TCP-gel placed thereon.

Figure 14:
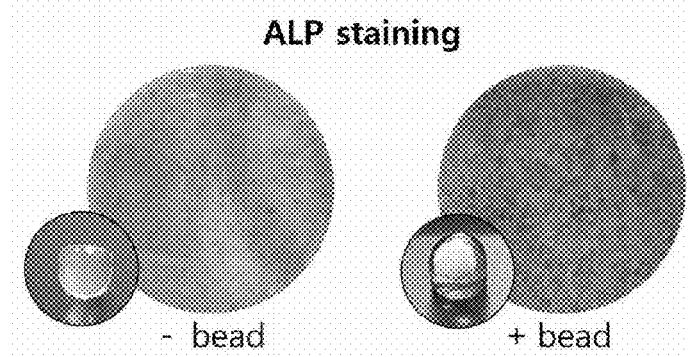
FIG. 14 shows photographs in which the osteogenic differentiation potential of a biogel and TCP hydrogel composite composition is confirmed by ALP staining.

Then, ALP staining was performed, and observations were made using a microscope. As a result, it was found that as the differentiation of osteoblasts progresses, the ALP expression was increased in the cells on day 7, and a further advance in ALP expression could be confirmed by staining. FIG. 14 is a photograph confirming the osteogenic differentiation potential of the biogel and TCP hydrogel scaffold, confirmed by ALP staining.

As shown in FIG. 14, it was found that compared to the group with no TCP hydrogel inside the biogel, the group with the TCP hydrogel inside the biogel was more strongly stained, showing a vivid purple color. That is, it could be seen that the TCP beads has an influence on the osteogenic differentiation of the surrounding cells.

The invention claimed is:

1. A method of preparing a hydrogel composition comprising:
    preparing a first composition by dissolving chitosan in an acidic solution containing gelatin;
    preparing a second composition by dispersing calcium phosphate in an acidic solution containing calcium chloride and then conducting sonication;
    preparing a mixed solution by mixing the first composition with the second composition; and
    preparing a hydrogel composition by adding dropwise the mixed solution into an alkaline solution.

2. The method of preparing a hydrogel composition of claim 1, wherein the hydrogel composition is a hydrogel bead composition.

3. The method of preparing a hydrogel composition of claim 1, wherein the chitosan is included in an amount of 0.1 wt % to 10 wt % in the first composition.

4. The method of preparing a hydrogel of claim 1, wherein the calcium phosphate is included in an amount of 0.1 wt % to 10 wt % in the second composition.

5. The method of preparing a hydrogel of claim 1, wherein the alkaline solution has a pH of 8 to 11.

6. The method of preparing a hydrogel of claim 1, wherein the alkaline solution is selected from a sodium hydroxide solution, a calcium hydroxide solution, and an ammonia solution.

* * * * *